United States Patent
Brgoch et al.

(10) Patent No.: US 10,948,411 B2
(45) Date of Patent: *Mar. 16, 2021

(54) BLUE EMITTING PERSISTENT PHOSPHOR COMPOSITIONS AS DIAGNOSTIC REPORTERS

(71) Applicant: University of Houston System, Houston, TX (US)

(72) Inventors: Jakoah Brgoch, Houston, TX (US); Erin Finley, Houston, TX (US); Andrew Paterson, Fremont, CA (US); Richard Willson, Houston, TX (US)

(73) Assignee: UNIVERSITY OF HOUSTON SYSTEM, Houston, TX (US)

(*) Notice: Subject to any disclaimer, the term of this patent is extended or adjusted under 35 U.S.C. 154(b) by 293 days.

This patent is subject to a terminal disclaimer.

(21) Appl. No.: 15/711,102

(22) Filed: Sep. 21, 2017

(65) Prior Publication Data

US 2018/0080874 A1 Mar. 22, 2018

Related U.S. Application Data

(60) Provisional application No. 62/397,556, filed on Sep. 21, 2016.

(51) Int. Cl.
| | |
|---|---|
| *G01N 21/64* | (2006.01) |
| *C09K 11/77* | (2006.01) |
| *G01N 33/58* | (2006.01) |
| *G01N 33/543* | (2006.01) |
| *G01N 21/84* | (2006.01) |

(52) U.S. Cl.
CPC ...... *G01N 21/6428* (2013.01); *C09K 11/7706* (2013.01); *C09K 11/7734* (2013.01); *C09K 11/7792* (2013.01); *G01N 21/8483* (2013.01); *G01N 33/543* (2013.01); *G01N 33/582* (2013.01); *G01N 2021/6439* (2013.01)

(58) Field of Classification Search
CPC ............ C09K 11/7706; C09K 11/7734; C09K 11/7792; G01N 2021/6439; G01N 21/6428; G01N 21/8483; G01N 33/543; G01N 33/582
See application file for complete search history.

(56) References Cited

U.S. PATENT DOCUMENTS

| | | | |
|---|---|---|---|
| 10,533,996 B2* | 1/2020 | Willson ............ | G01N 21/6428 |
| 2015/0105284 A1 | 4/2015 | Willson et al. | |

FOREIGN PATENT DOCUMENTS

| CN | 102775985 A | 11/2012 |
|---|---|---|
| CN | 103938297 A | 7/2014 |
| CN | 103172356 B | 5/2015 |
| CN | 104762081 A | 7/2015 |

OTHER PUBLICATIONS

Finley et al., "Optimizing Blue Persistent Luminescence in (Sr1-δBaδ)2MgSi2O7:Eu2+,Dy3+ via Solid Solution for Use in Point-of-Care Diagnostics," ACS Appl. Mater. Interfaces, 2016, vol. 8, No. 40, pp. 26956-26963; Publication Date: Sep. 16, 2016.*

Paterson et al., "Persistent Luminescence Strontium Aluminate Nanoparticles as Reporters in Lateral Flow Assays," Anal. Chem., 2014, vol. 86, No. 19, pp. 9481-9488; Publication Date: Sep. 23, 2014.*

P. Dorenbos, "Mechanism of persistent luminescence in Sr2MgSi2O7:Eu2+,Dy3+", Physica status solidi (b), 2005, 242, R7-R9.

M. Ardit, M. Dondi, M. Merlini, G. Cruciani, "Melilite-type and melilite-related compounds: structural variations along the join (Sr2-xBax)MgSi2O7 (0≤x≤2) and high-pressure behavior of the two end-members", Physics and Chemistry of Minerals, 2012, 39, 199-211.

C. Zhang, X. Gong, C. Deng, "The phase transition of color-tunable long afterglow phosphors Sr1.94—xBaxMgSi2O7:Eu2+,Dy3+", Journal of Alloys and Compounds, 2016, 657, 436-442.

Lin, Y., Tang, Z., Zhang, Z., Wang, X., Zhang, J., "Preparation of a new long afterglow blue-emitting Sr2MgSi2O7-based photoluminescent phosphor", J. Mater. Sci. Lett. 2001, 20, 1505-1506.

Hermi F. Brito, Jorma Hölsä, Högne Jungner, Taneli Laamanen, Mika Lastusaari, Marja Malkamäki, and Lucas C.V. Rodrigues, "Persistent luminescence fading in Sr2MgSi2O7:Eu2+,R3+ materials: a thermoluminescence study," Opt. Mater. Express 2, 287-293 (2012).

Kwon, K. H., Im, W. B., Jeon, D. Y., "Energy transfer in Sr2MgSi2O7: Eu2+ phosphors in nano scale and their application to solid state lighting with excellent color rendering", Journal of Nanoscience and Nanotechnology, 2013, 13, 4079-4083.

* cited by examiner

Primary Examiner — Galina M. Yakovleva

(74) Attorney, Agent, or Firm — Winstead PC

(57) ABSTRACT

Disclosed are methods of detecting one or more analytes in a sample by: (1) associating the sample with a surface that includes an analyte binding agent to result in the immobilization of the analytes on the surface; (2) contacting the analyte with a composition that includes at least one phosphor compound with an affinity for the analyte; (3) formation of immobilized analyte binding agent-analyte-phosphor complexes on the surface; (4) separating unbound phosphor compounds from the immobilized complexes; (5) detecting a presence or absence of a luminescence signal from the immobilized complexes; and (6) correlating the luminescence signal to the presence or absence of the analyte in the sample. The phosphor compound may include $(Sr_{1-\delta}Ba_\delta)_{2-j-k}MgSi_2O_7:Eu_jDy_k$, $(Sr_{1-\delta}Ba_\delta)_{2-x}MgSi_2O_7:Eu^{2+}Dy^{3+}$, $(Sr_{1-\delta}Ba_\delta)_2MgSi_2O_7:Eu^{2+}Dy^{3+}$, $(Sr_{1-\delta}Ba_\delta)_{2-x}MgSi_2O_7:Eu^{2+}$, and combinations thereof. Additional phosphor compounds may also be utilized, such as $[AE]_2MgSi_2O_7:Eu^{2+}$, $[AE]Al_2O_4:Eu^{2+}$, $Dy^{3+}$, and combinations thereof, where AE is at least one of Ca, Sr, or Ba.

34 Claims, 17 Drawing Sheets

FIG. 7A
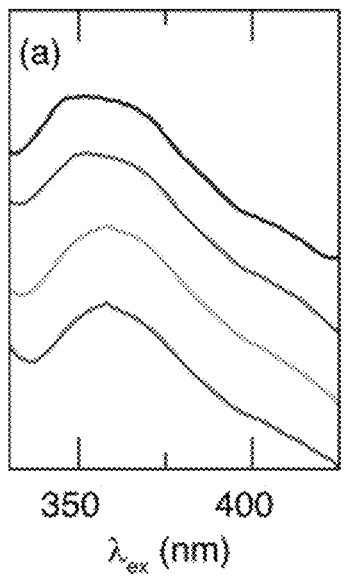
FIG. 7B
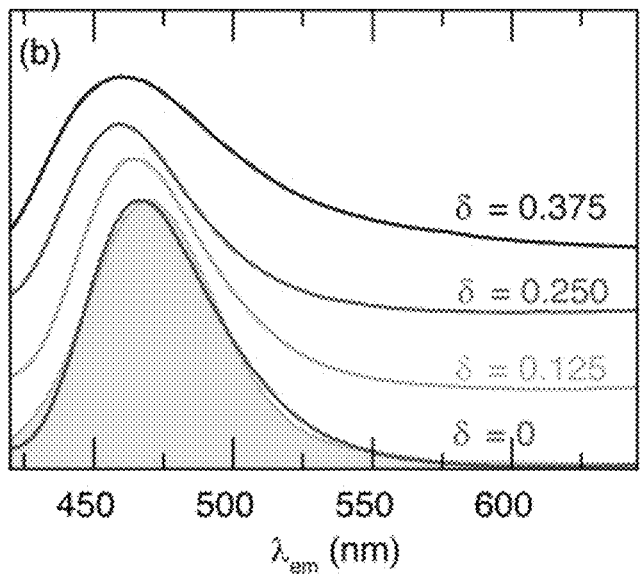
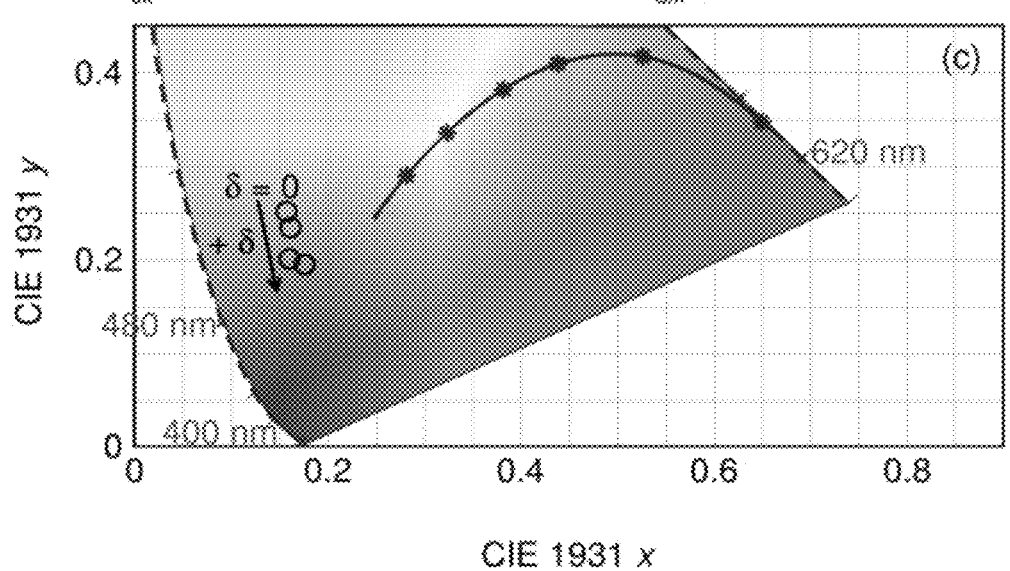
FIG. 7C

FIG. 9C
FIG. 9D
FIG. 9E
FIG. 9F
FIG. 9G
FIG. 9H $T$ (K)

BLUE EMITTING PERSISTENT PHOSPHOR COMPOSITIONS AS DIAGNOSTIC REPORTERS

CROSS-REFERENCE TO RELATED APPLICATIONS

This application claims priority to U.S. Provisional Patent Application No. 62/397,556, filed on Sep. 21, 2016. The entirety of the aforementioned application is incorporated herein by reference.

STATEMENT REGARDING FEDERALLY SPONSORED RESEARCH

Not applicable

BACKGROUND

Various tests and detection methodologies are used for specifically detecting numerous types of analytes in different applications such as medical diagnostics, food safety, quality assurance, and environmental monitoring. Current methods and systems for utilizing analytical reporters have numerous limitations in terms of cost, efficiency, sensitivity, versatility and deployability in low-resource settings. Therefore, more effective technologies and sensing methods are desired to overcome these limitations.

SUMMARY

In some embodiments, the present disclosure pertains to methods of detection of at least one analyte of interest in a sample by methods that include one or more of the following steps: (1) associating the sample with a surface that includes an analyte binding agent to result in the immobilization of at least some of the analytes present in the sample on the surface; (2) contacting the analyte present in the sample with a composition that includes at least one phosphor compound that has an affinity for the analyte; (3) formation of immobilized analyte binding agent-analyte-phosphor complexes on the surface; (4) separating the unbound phosphor compounds from the immobilized complexes; (5) detecting a presence or absence of a luminescence signal from the immobilized complexes; and (6) correlating the luminescence signal to the presence or absence of the analyte in the sample.

In some embodiments, the phosphor compound includes, without limitation, $(Sr_{1-\delta}Ba_\delta)_{2-j-k}MgSi_2O_7:Eu_jDy_k$, $(Sr_{1-\delta}Ba_\delta)_{2-x}MgSi_2O_7:Eu^{2+}Dy^{3+}$, $(Sr_{1-\delta}Ba_\delta)_2MgSi_2O_7:Eu^{2+}Dy^{3+}$, $(Sr_{1-\delta}Ba_\delta)_{2-x}MgSi_2O_7:Eu^{2+}$, and combinations thereof. In some embodiments, $\delta$ is between 0 and 0.5, j and k are greater than about 0.0005 and less than about 0.3, and x is an integer between 0 and 1.

In some embodiments, the composition includes additional phosphor compounds. In some embodiments, the additional phosphor compound is a non-blue-emitting persistent phosphor compound, such as a green-emitting or blue-green emitting persistent phosphor compound. In some embodiments, the additional phosphor compound is a blue-emitting persistent phosphor compound. In some embodiments, the additional phosphor compound includes, without limitation, $[AE]_2MgSi_2O_7:Eu^{2+}$, $[AE]Al_2O_4:Eu^{2+}$, $Dy^{3+}$, and combinations thereof. In some embodiments, AE is at least one of Ca, Sr, or Ba.

In the analyte to be detected includes, without limitation, nucleotides, proteins, peptides, small molecules, antigens, DNA strands, oligonucleotides, metals, metal ions, and combinations thereof. In some embodiments, the method is utilized to detect a single analyte in the sample. In some embodiments, the method is utilized to detect multiple analytes in the sample. In some embodiments, the surface includes analyte binding agents for each of the analytes to be detected in the sample. In some embodiments, the composition includes a plurality of different phosphor compounds that each have a specific affinity for an analyte to be detected in the sample.

In some embodiments, the detection of analytes occurs by exciting the phosphor compound with a light source and detecting the emitted luminescence signal from the excited phosphor compound. In some embodiments, the absence of the luminescence signal indicates the absence of the analyte from the sample, and the presence of the luminescence signal indicates the presence of the analyte in the sample.

BRIEF DESCRIPTION OF THE FIGURES

FIGS. 7A, 7B and 7C show the excitation spectra (FIG. 7A), the emission spectra (FIG. 7B), and the Gaussian fit diagram (FIG. 7C) for $(Sr_{1-\delta}Ba_\delta)_2MgSi_2O_7:Eu^{2+}$, $Dy^{3+}$ ($\delta=0$, 0.125, 0.250, 0.375). Emission spectra were collected at $\lambda=365$ nm and the excitation spectra were collected at the $\lambda_{max}$ of emission spectrum for each sample. The Gaussian fit is solid gray. The CIE diagram in FIG. 7C shows blue shift across the solid solution.

FIGS. 9A-H show thermoluminescence peaks and the corresponding temperatures for $(Sr_{1-\delta}Ba_\delta)_{2-x}MgSi_2O_7$ ($\delta=0$, 0.125, 0.250, 0.375). $Eu^{2+}$ only is shown for plots in FIGS. 9A, 9C, 9E, and 9G while $Eu^{2+}$, $Dy^{3+}$ is shown as plots in FIGS. 9B, 9D, 9F, and 9H.

DETAILED DESCRIPTION

Figure 1A:
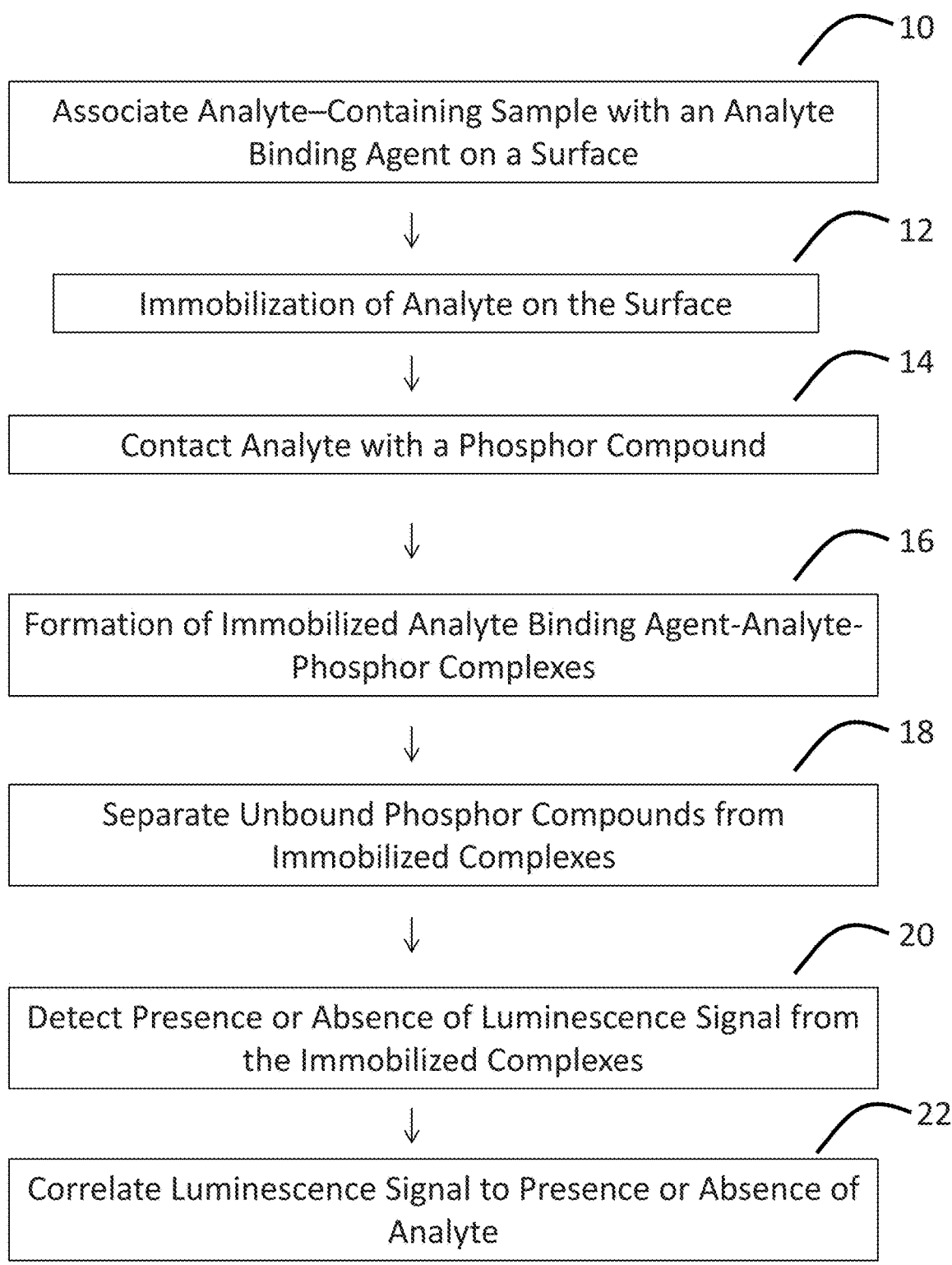
FIGS. 1A-1D provide a scheme of a method of detecting an analyte in a sample (FIG. 1A) and assays for facilitating the detection (FIGS. 1B-1D).

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Unless defined otherwise, all technical and scientific terms used herein have the meaning commonly understood by a person skilled in the art to which the invention belongs. The following references provide one of skill with a general definition of many of the terms used in this disclosure: Singleton et al., Dictionary of Microbiology and Molecular Biology (2nd ed. 1994); The Cambridge Dictionary of Science and Technology (Walker ed., 1988); The Glossary of Genetics, 5th ed., R. Reigers et al. (eds.), Springer Verlag (1991); Hale & Marham, The Harper Collins Dictionary of Biology (1991); and Solid State Chemistry: An Introduction, $4^{th}$ ed. by Smart and Moore, CRC Press (2012).

In the present disclosure, the terms "phosphorescence", "phosphorescent", and phosphor refer to inorganic, ceramic, or crystalline solid material, unless specifically stated otherwise. In the present disclosure, the terms "phosphorescence", "long-term phosphorescence", and "persistent luminescence", are all terms used interchangeably to describe the phenomenon in which an inorganic, ceramic, or crystalline solid material, emits light for long periods of time, in the order of microseconds to hours, after stimulation with an energy source.

Many technologies and assay formats in biosensing and analytical chemistry involve the use of reporters or labels to transduce the specific binding of an analyte to a molecular recognition moiety into an observable signal. The analytical sensitivity or limit of detection of an assay, therefore, depends strongly on the detectability of the signal generated by the reporter. Reporter technologies vary broadly in composition and the mechanisms of signal generation, which affects sensitivity, linearity, and stability, making some classes of reporters better suited to particular applications than others.

Prior reporter technologies possess multiple problems that prohibit their widespread adoption in point-of-care settings. Enzymes are prone to denaturation, leading to loss in activity over time. Furthermore, many enzymes use substrates that require refrigeration or storage conditions that are not amenable to field use. Almost all fluorescent dyes are prone to photobleaching, and many are prone to chemical degradation.

Persistent luminescence nanoparticles or microparticles that emit light for several milliseconds to several hours after excitation present a new and potentially vast improved way to design qualitative and quantitative assays with luminescence readout and enhanced sensitivity due to significantly lower background autofluorescence, and with minimal optical hardware. Additionally, inorganic persistent luminescence nanoparticles are typically much more resistant to photobleaching than fluorescent dyes, phosphorescent organic and organometallic dyes or compounds, and even quantum dots.

Persistent luminescence (PersL) in inorganic phosphors is an optical phenomenon that provides a pathway for visible or infrared photon emission to occur for several seconds to hours after photoexcitation. The emission lifetimes of these compounds are orders of magnitude longer than the spin-forbidden transitions in phosphorescent organic fluorophores or metal-chelate molecules. This makes the aforementioned compounds ideal for "glow-in-the-dark" applications, such as safety signs, emergency displays, luminescent paints, and, more recently, as optical reporters in biological applications.

Persistent luminescence has been studied at great length to understand the mechanism in which a material is excited with a high energy light source followed by photon emission that can last for seconds to hours. Persistent luminescence involves a photoexcitation of charge carriers (e.g., electrons and/or holes), which simultaneously fluoresce from electronic transitions on the luminescence center as well as populate (defect) trap states. The subsequent interaction between the luminescence center and the slow release of charge carriers trap states, as mediated by thermal activation through the material's electronic band-gap, gives rise to luminescence lifetimes of more than 10 hours after photoexcitation.

Inorganic persistent phosphors have also been applied as optical reports in a lateral flow assay (LFA) as an alternative to traditional organic fluorophores or gold nanoparticles. Unfortunately, only a few compounds like alkaline earth aluminates possess such long luminescence lifetimes. Furthermore, most of the aforementioned compounds decompose in aqueous environments, thereby limiting their application as reporters in biological assays. Currently, the green emitting $SrAl_2O_4: Eu^{2+}, Dy^{3+}$ is the most widely used compound.

Smartphone-based bio-sensing technology has since been developed with the use of persistent phosphors, thereby allowing more sensitive point-of-care diagnostics. These devices also use $SrAl_2O_4:Eu^{2+}, Dy^{3+}$ as the reporter because its luminescent lifetime and intensity enable optimal detection sensitivity with a smartphone camera. However, alkaline earth aluminates tend to degrade in aqueous environments and require encapsulation of particles in a water-resistant barrier prior to use in most bio-sensing applications. Therefore, there exists a need in the art for developing persistent phosphors that overcome the aforementioned disadvantages and that can be utilized in diverse applications, including biological and environmental applications.

The development of alternative persistent phosphors may not only allow the replacement of $SrAl_2O_4:Eu^{2+}, Dy^{3+}$ in some applications, but if the emission color is sufficiently distinct, it may also provide a pathway for creating multiplexed assays. Dual reporter systems are increasingly used in diagnostics for several reasons, including enabling healthcare providers to better diagnose diseases that manifest with similar symptoms, decreasing sampling error, and lowering cost by detecting multiple analytes in parallel in a single test.

Alkaline earth silicates are one category of persistent luminescent materials that have the added advantage of chemical stability that is lacking in the alkaline earth aluminates. The series of silicates, $AE_2MgSi_2O_7:Eu^{2+}$ (AE=Ca, Sr, Ba) that crystallize in the Åkermanite-type structure have all been reported as efficient phosphors. The $Ba^{2+}$ forms in the monoclinic space group C2/c (no. 15) while the $Ca^{2+}$ and $Sr^{2+}$ analogues are isostructural and form in tetragonal space group $P\bar{4}2_1m$ (no. 113). The most prominent compositions out of these phases for persistent luminescence are $Ca_2MgSi_2O_7:Eu^{2+}$ and $Sr_2MgSi_2O_7:Eu^{2+}$, which produce respective emissions in the blue (470 nm) and green (535 nm) regions of the visible spectrum.

Preparing a solid solution between $Ca^{2+}$ and $Sr^{2+}$ shows that the emission wavelength is tunable and the persistent luminescent lifetimes (PersL) can be enhanced when co-substituted with $Dy^{3+}$. $Sr_2MgSi_2O_7:Eu^{2+}, Dy3^+$ has since been optimized to push the persistent luminescent lifetime in excess of 10 hours. $Ca_2MgSi_2O_7:Eu^{2+},Tb^{3+}$ and $Ba_2MgSi_2O_7:Eu^{2+}, Tm^{3+}$ also show PersL with a reported lifetime greater than 5 hours. Considering the long lifetimes and blue-green emission, these disilicate compounds are ideal targets as alternative persistent luminescent materials.

In some embodiments, the present disclosure pertains to methods for detection of at least one analyte of interest in a sample. In some embodiments illustrated in FIG. 1A, the methods of the present disclosure can include one or more of the following steps of: associating the sample with a surface that includes an analyte binding agent (step 10) to result in the immobilization of at least some of the analytes present in the sample on the surface (step 12); contacting the analyte present in the sample with a composition that includes at least one phosphor compound with an affinity for the analyte (step 14) to result in the formation of immobilized analyte binding agent-analyte-phosphor complexes on the surface (step 16); separating the unbound phosphor compounds from the immobilized complexes (step 18); detecting a presence or absence of a luminescence signal from the immobilized complexes (step 20); and correlating the luminescence signal to the presence or absence of the analyte in the sample (step 22). In some embodiments, the methods of the present disclosure occur without a separation step (i.e., step 18).

In some embodiments, the methods of the present disclosure can be utilized to detect a single analyte in a sample. In some embodiments, the methods of the present disclosure can be utilized to detect multiple analytes in a sample in parallel, such as by utilizing surfaces with multiple analyte binding agents for each of the analytes to be detected, and compositions with a plurality of different phosphor compounds that are each specific for an analyte to be detected.

Figure 1B:
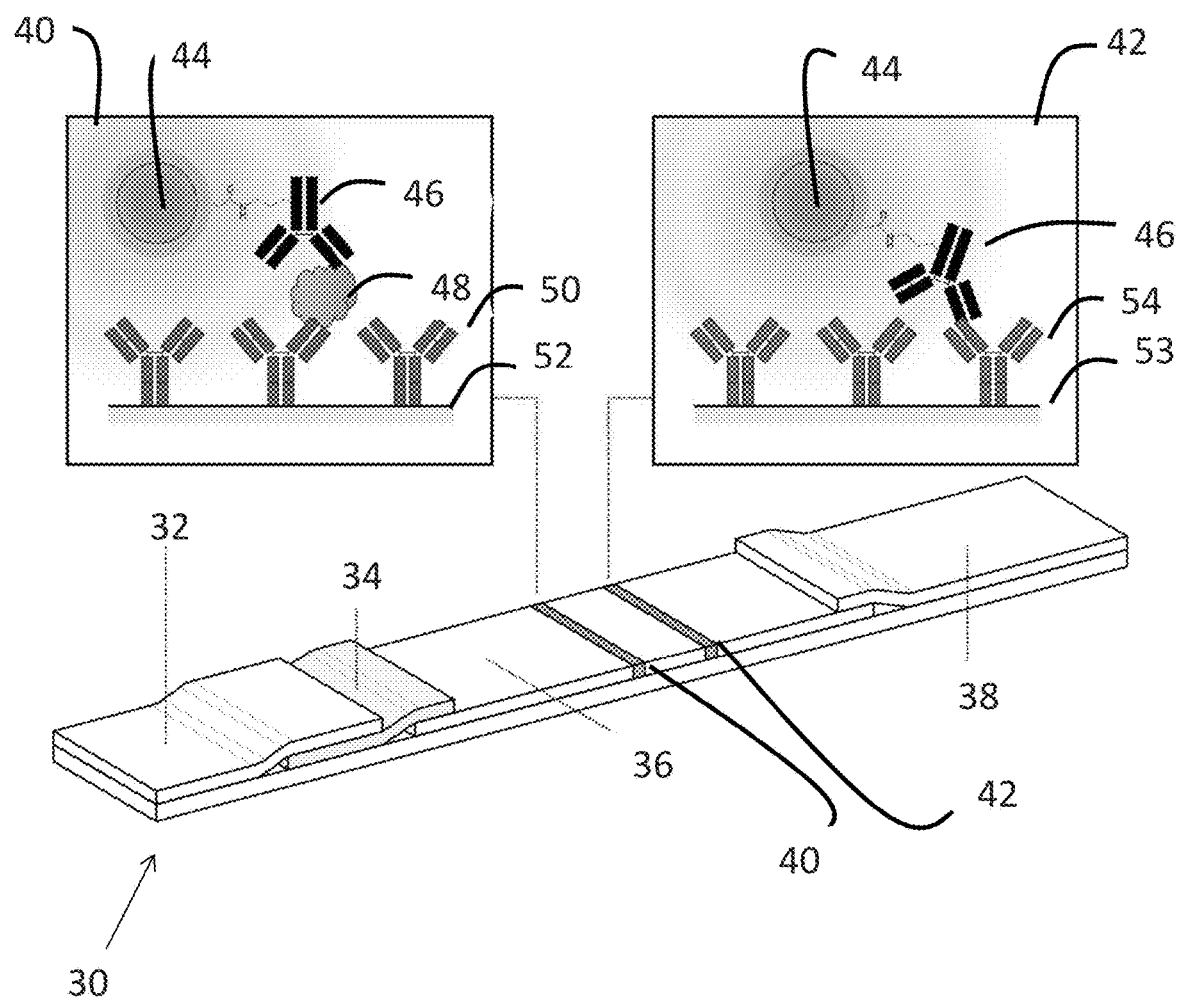

The methods of the present disclosure can be practiced in various manners. For instance, as illustrated in FIG. 1B, cartridge 30 containing sample pad 32, conjugate pad 34, membrane 36, first channel 40, second channel 42, and adsorbent pad 38 may be utilized to practice the methods of the present disclosure. In this embodiment, first channel 40 has surface 52 with analyte binding agent 50. Likewise, second channel 42 has surface 53 with control binding agent 54. In operation, a sample containing analyte 48 is associated with analyte binding agent 50 in first channel 40 and control binding agent 54 in second channel 42. Thereafter, a composition with phosphor compound 44 that is linked to analyte binding agent 46 is contacted with first channel 40 and second channel 42. This results in the formation of immobilized analyte binding agent-analyte-phosphor complexes in first channel 40 and control complexes in second channel 42. After the separation of unbound phosphor compounds from the immobilized complexes, the presence or absence of a luminescence signal from the immobilized complexes is detected and correlated to the presence or absence of analytes 48 in the sample.

Figures 1, 1C:
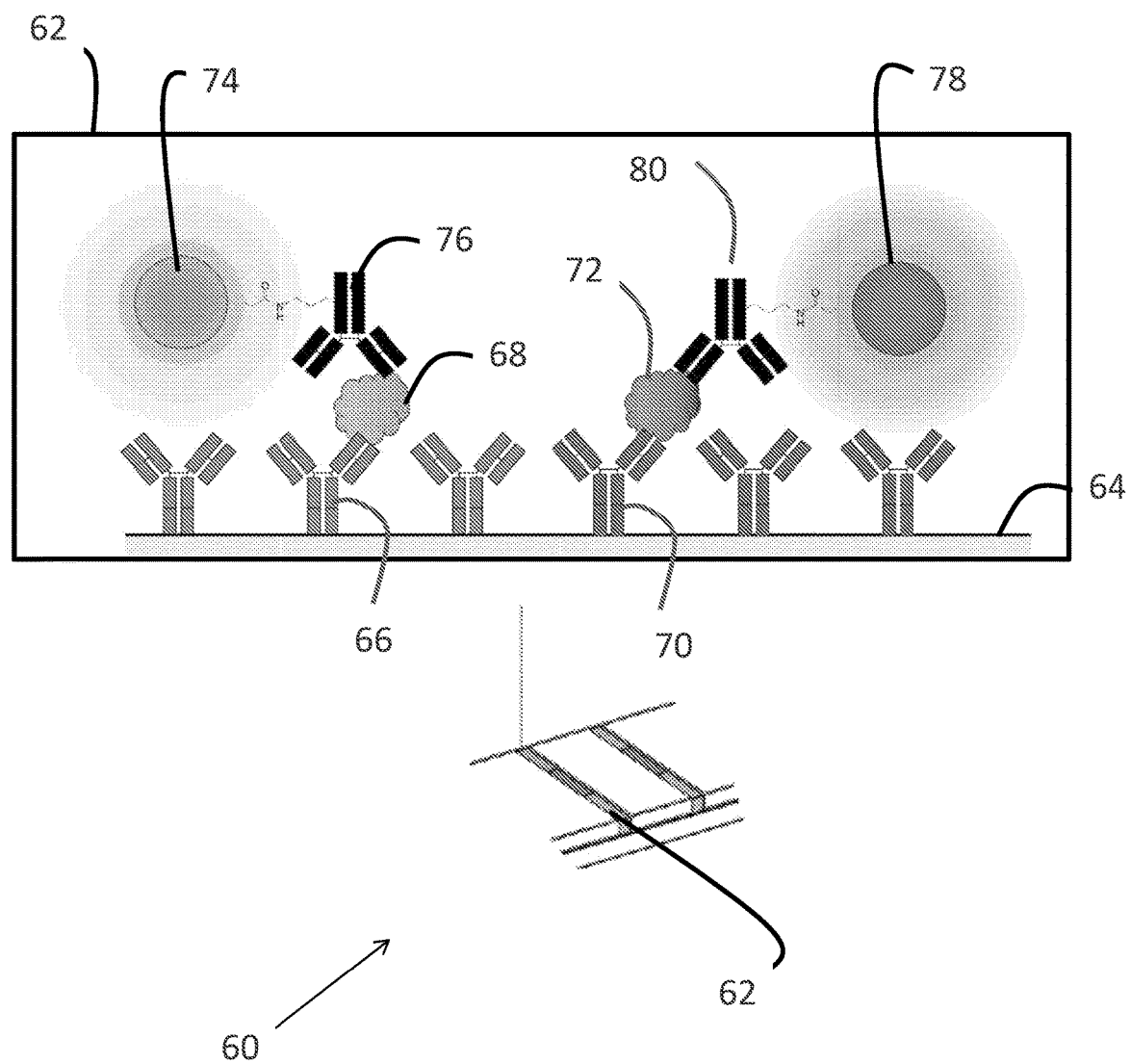
Figures 1, 1C, 2:
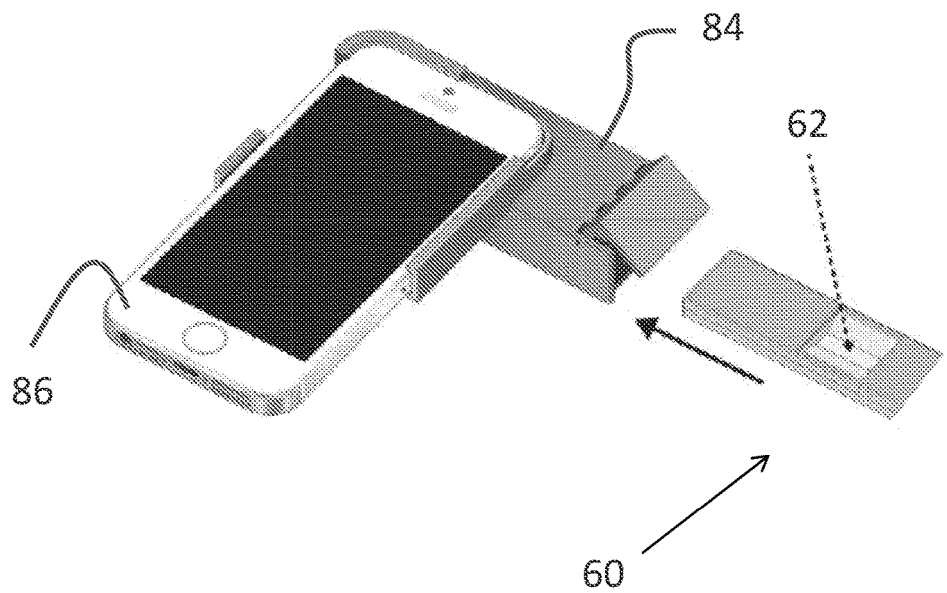

Another embodiment of a first channel 40 is illustrated in FIG. 1C-2 as first channel 62 of cartridge 60. In this embodiment, first channel 62 has surface 64 with analyte binding agent 66 specific for analyte 68, and analyte binding agent 70 specific for analyte 72. In operation, a sample that may contain both analytes 68 and 72 is associated with analyte binding agents 66 and 70 in first channel 62. Thereafter, a composition with phosphor compound 78 that is linked to analyte binding agent 80 specific for analyte 72 and additional phosphor compound 74 that is linked to analyte binding agent 76 specific for analyte 68 is contacted with first channel 62. This results in the formation of immobilized analyte binding agent-analyte-phosphor complexes.

Figure 1D:
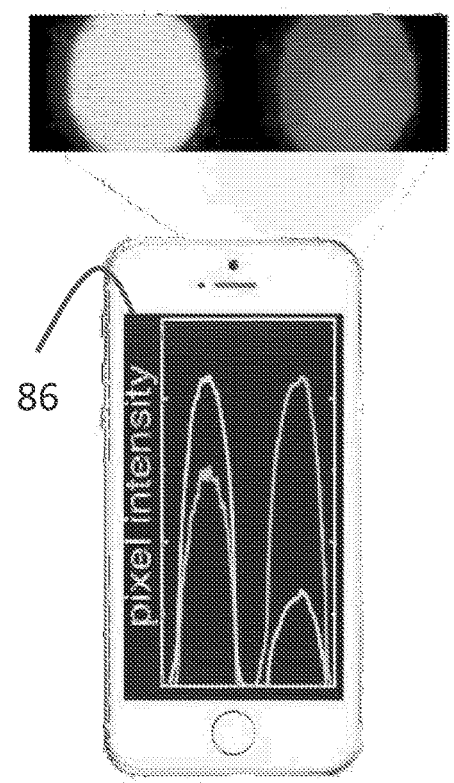

After the separation of unbound phosphor compounds from the immobilized complexes, the presence or absence of a luminescence signal from the immobilized complexes is detected and correlated to the presence or absence of analytes 68 and 72 in the sample. For instance, as illustrated in FIGS. 1C-1-1D, cartridge 60 can be placed in smartphone 86 through adaptor 84. Thereafter, the smartphone's light source flashes light on second channel 62 so that phosphor compounds 74 and 78 are excited. The emission from each of phosphor compounds 74 and 78 are then correlated to the presence of analytes 68 and 72, respectively.

As set forth in more detail herein, the methods of the present disclosure can have various embodiments. For instance, various methods may be utilized to associate various samples with various surfaces that include various analyte binding agents. Likewise, various methods may be utilized to contact the analytes present in the samples with various compositions that include various phosphor compounds. Moreover, various methods may be utilized to separate the unbound phosphor compounds from the immobilized complexes, detect the presence or absence of a luminescence signal from the immobilized complexes, and correlate the presence or absence of the luminescence signal to the presence or absence of analytes in the sample.

Analytes

The methods of the present disclosure can be utilized to detect various analytes. For instance, in some embodiments, the analytes include, without limitation, organic analytes, inorganic analytes, aqueous analytes, and combinations thereof. In some embodiments, the analytes include, without limitation, nucleotides, proteins, peptides, small molecules, antigens, DNA strands, oligonucleotides, metals, metal ions, and combinations thereof.

The analytes of the present disclosure may be in various forms. For instance, in some embodiments, the analyte is in the form of at least one of liquids, gases, solids, and combinations thereof. In some embodiments, the analyte is in the form of a liquid.

The analytes of the present disclosure may be derived from various samples. For instance, in some embodiments, the sample is a biological sample. In some embodiments, the sample is a biological specimen, such as a tissue. In some embodiments, the sample includes a single analyte to be detected. In some embodiments, the sample includes a plurality of different analytes to be detected.

In some embodiments, the analytes of the present disclosure may be derived from liquid samples. In some embodiments, the analytes of the present disclosure may include metals or metal ions (e.g., metal contaminants) in a liquid sample. In some embodiments, the liquid samples may be water samples or aqueous solutions.

Phosphor Compounds

The methods of the present disclosure may utilize various types of phosphor compounds. For instance, in some embodiments, the phosphor compounds include a blue-emitting persistent phosphor compound. In some embodiments, the phosphor compound includes, without limitation, $(Sr_{1-\delta}Ba_\delta)_{2-j-k}MgSi_2O_7:Eu_jDy_k$, $(Sr_{1-\delta}Ba_\delta)_{2-x}MgSi_2O_7:Eu^{2+}Dy^{3+}$, $(Sr_{1-\delta}Ba_\delta)_2MgSi_2O_7:Eu^{2+}Dy^{3+}$, $(Sr_{1-\delta}Ba_\delta)_{2-x}MgSi_2O_7:Eu^{2+}$, and combinations thereof.

In some embodiments, $\delta$ is between 0 and 0.5. In some embodiments, $\delta$ is more than 0 but less than 0.5. In some embodiments, $\delta$ is at least one of 0, 0.125, 0.25, or 0.375. In some embodiments, $\delta$ is 0.375.

In some embodiments, j and k are greater than about 0.0005 and less than about 0.3. In some embodiments, x is an integer between 0 and 1. In some embodiments, x is 0.

In some embodiments, the phosphor compound is $(Sr_{1-\delta}Ba_\delta)_{2-j-k}MgSi_2O_7:Eu_jDy_k$. In some embodiments, the phosphor compound is $(Sr_{0.625}Ba_{0.375})_2MgSi_2O_7:Eu^{2+}$. In some embodiments, the phosphor compound is $(Sr_{0.625}Ba_{0.375})_2MgSi_2O_7:Eu^{2+}, Dy^{3+}$.

The methods of the present disclosure may also utilize additional phosphor compounds. For instance, in some embodiments, the additional phosphor compound is a blue-emitting persistent phosphor compound. In some embodiments, the additional phosphor compound is a non-blue-emitting persistent phosphor compound. In some embodiments, the additional phosphor compound is a green-emitting persistent phosphor compound.

In some embodiments, the additional phosphor compound includes, without limitation, $[AE]_2MgSi_2O_7:Eu^{2+}$, $[AE]Al_2O_4:Eu^{2+}, Dy^{3+}$, and combinations thereof. In some embodiments, AE is at least one of Ca, Sr, or Ba.

In some embodiments, the additional phosphor compound includes $Sr_2MgSi_2O_7:Eu^{2+}$. In some embodiments, the additional phosphor compound is $SrAl_2O_4:Eu^{2+}, Dy^{3+}$. In more specific embodiments, the phosphor compound is $(Sr_{1-\delta}Ba_\delta)_2MgSi_2O_7:Eu^{2+}$, and the additional phosphor compound is $SrAl_2O_4:Eu^{2+}, Dy^{3+}$. In some embodiments, the phosphor compound is $(Sr_{0.625}Ba_{0.375})_2MgSi_2O_7:Eu^{2+}, Dy^{3+}$ and the additional phosphor compound is $SrAl_2O_4:Eu^{2+}, Dy^{3+}$.

In some embodiments, the optical signature of each of the phosphor compounds is unique. For instance, in some embodiments, the blue-emitting $(Sr_{0.625}Ba_{0.375})_2MgSi_2O_7:Eu^{2+}, Dy^{3+}$ and the green-emitting $SrAl_2O_4:Eu^{2+}, Dy^{3+}$ in a single lateral flow assay shows that these two compounds can be detected and resolved simultaneously.

The phosphor compounds of the present disclosure may be in various forms. For instance, in some embodiments, the phosphor compounds of the present disclosure may be in the form of a solid solution. In some embodiments, the phosphor compounds of the present disclosure may be in the form of particles. In some embodiments, the particles include, without limitation, nanoparticles, microparticles, and combinations thereof. In some embodiments, the particles have sizes of at least about 1000 nm. In some embodiments, the particles have sizes of less than about 1000 nm. In some embodiments, the particles have sizes ranging from about 50 nm to about 1000 nm. In some embodiments, the particles have sizes of about 600 nm, about 400 nm, about 300 nm, about 200 nm, about 100 nm, or about 50 nm.

The phosphor compounds of the present disclosure may also include additional molecules or moieties. In some embodiments, the additional molecules or moieties may be covalently attached to the phosphor compounds. In some embodiments, the additional molecules or moieties may be non-covalently attached to the phosphor compounds, such as by physical adsorption.

In some embodiments, the phosphor compounds of the present disclosure may be associated with one or more linkers. In some embodiments, the linkers are capable of bonding with a surface (e.g., a silica surface). In some embodiments, the linkers include, without limitation, reactive silane-based linkers, triethoxysilylbutyraldehyde (TESBA), poly (ethylene glycol) (PEG), (3-aminopropyl) triethoxysilane (APTES), alkanes, and combinations thereof.

In some embodiments, the phosphor compounds of the present disclosure may include reactive silane linkers that bond with a silica surface and also have functional groups for coupling to other molecules. In some embodiments, commercially available trialkoxysilanepolyethylene glycol molecules with reactive functional groups for coupling to proteins can be directly attached to an inorganic silica or alumina surface on a phosphor compound. In some embodiments, linkers may be conjugated to a phosphor compound before, during or after coating the phosphor compound with water soluble moieties. For instance, in some embodiments, phosphor compounds may be coated with a reactive silane and subsequently conjugated with polyethylene glycols.

In some embodiments, the phosphor compounds of the present disclosure may be associated with one or more functional groups. In some embodiments, the functional groups are capable of binding to analyte binding agents on a surface. In some embodiments, the functional groups include, without limitation, amine groups, carboxyl groups, aldehydes, ketones, hydroxyls, thiols, hydrazides, anhydrides, alkenes, alkynes, azides, and combinations thereof.

In some embodiments, the phosphor compounds of the present disclosure may be associated with one or more analyte binding agents (e.g., analyte binding agent 46, as shown in FIG. 1B). In some embodiments, the analyte binding agent includes, without limitation, antibodies, aptamers, haptens, DNA strands, oligonucleotides, and combinations thereof.

In more specific embodiments, functional groups can be directly coupled to aldehydes on antibodies created by oxidizing the polysaccharides on the $F_c$ portion of the antibody with periodate. In further embodiments, Protein A or other proteins that bind specifically to the $F_c$ portion of an antibody can be attached to a phosphor compound and then be used to bind to an antibody in an oriented manner to improve the binding efficiency of the phosphor compound to an analyte.

The phosphor compounds of the present disclosure can have various properties. For instance, in some embodiments, the phosphor compounds of the present disclosure have long luminescence lifetimes. In some embodiments, the phosphor compounds of the present disclosure have luminescence lifetimes of more than 10 minutes. In some embodiments, the phosphor compounds of the present disclosure have luminescence lifetimes of more than 1 hour.

In some embodiments, the phosphor compounds of the present disclosure have tunable emission wavelengths. In some embodiments, the emission wavelengths are incrementally shifted from blue-green wavelength to near-UV wavelength. In some embodiments, the emission wavelengths of the phosphor compounds are minimized in the green region of the visible spectrum. In some embodiments, the emission wavelengths of the phosphor compounds of the present disclosure can be tuned by varying the composition of the phosphor compound (e.g., the $\delta$ value).

In some embodiments, the phosphor compounds of the present disclosure absorb light in the ultraviolet (UV) to near UV region (~365 nm to 410 nm) and re-emit the absorbed light in the blue region (~440 nm to ~475 nm) of the electromagnetic spectrum. In some embodiments, the phosphor compounds of the present disclosure have efficient photoluminescence when excited between 365 nm and 435 nm. In some embodiments, the phosphor compounds of the present disclosure have a high photoluminescence quantum yield.

The phosphor compounds of the present disclosure may be in various compositions in various forms. For instance, in some embodiments, the phosphor compounds of the present disclosure may be in a composition in the form of a solution.

Surfaces

The methods of the present disclosure may utilize various surfaces. For instance, in some embodiments, the surface is in the form of at least one of microfluidic chips, paper microfluidics, membranes, microplates, microbubbles for flotation, transparent surfaces, particles, and combinations thereof. In some embodiments, the surface may be in the form of particles, such as beads.

In some embodiments, the surface is part of a lateral flow assay, such as a lateral flow assay on a cartridge (e.g., surfaces 52 and 53 in FIG. 1B and surface 64 in FIG. 1C-1). The utilization of additional surfaces can also be envisioned.

The surfaces of the present disclosure may be associated with various types of analyte binding agents. For instance, in some embodiments, the analyte binding agents include, without limitation, antibodies, aptamers, haptens, DNA strands, oligonucleotides, and combinations thereof. In some embodiments, the analyte binding agents include antibodies. In some embodiments, the analyte binding agents may bind to metals or metal ions, such as metals or metal ions in a liquid sample. In some embodiments, the analyte binding agents may bind to proteins or peptides, such as proteins or peptides in a biological sample.

In some embodiments, the surfaces of the present disclosure include analyte binding agents that are specific for a single type of analyte (e.g., analyte binding agent 50 specific for analyte 48, as shown in FIG. 1B). In some embodiments, the surfaces of the present disclosure include multiple analyte binding agents that are each specific for a specific analyte (e.g., analyte binding agent 66 specific for analyte 68, and analyte binding agent 70 specific for analyte 72, as shown in FIG. 1C-1).

Formation of Analyte Binding Agent-Analyte-Phosphor Complexes

Various methods may be utilized to form analyte binding agent-analyte-phosphor complexes on surfaces. In particular, various methods may be utilized to associate analyte-containing samples with an analyte binding agent on a surface. Likewise, various methods may be utilized to contact analytes with phosphor compound containing compositions.

For instance, in some embodiments, each of the associating step and the contacting step can occur by methods that include, without limitation, mixing, incubating, swapping, dipping, flowing, and combinations thereof. In some embodiments, the associating step occurs by flowing the sample through the surface while the contacting step occurs by mixing the sample with the composition.

The associating and contacting steps can occur at various times. For instance, in some embodiments, the associating step and the contacting step occur simultaneously. In some embodiments, the associating step occurs before the contacting step. In some embodiments, the contacting step occurs before the associating step.

Separation of Unbound Phosphor Compounds

Various methods may also be utilized to separate unbound phosphor compounds from immobilized analyte binding agent-analyte-phosphor complexes. For instance, in some embodiments, the separation occurs by washing away at least some of the unbound phosphor compounds from the immobilized complexes. In some embodiments, the separation occurs by centrifugation of surfaces containing immobilized complexes from the unbound phosphor compounds. In some embodiments, the separation occurs by decanting the unbound phosphor compounds from the immobilized complexes.

Detection of a Luminescence Signal

Various methods may also be utilized to detect the presence or absence of a luminescence signal from immobilized complexes. For instance, in some embodiments, the detection occurs by exciting the phosphor compound with a light source and detecting the emitted luminescence signal from the excited phosphor compound.

The phosphor compounds of the present disclosure may be excited with various light sources. For instance, in the some embodiments, the phosphor compound is excited with a solid-state (e.g., LED-based) white light source. In some embodiments, the light source may be derived from a smart phone-based flash.

The phosphor compounds of the present disclosure may be excited at various wavelengths. For instance, in some embodiments, the phosphor compounds of the present disclosure are excited at wavelengths ranging from about 365 nm to about 435 nm. In some embodiments, the phosphor compounds of the present disclosure are excited at wavelengths ranging from about 365 nm to about 410 nm.

The phosphor compounds of the present disclosure can emit luminescence signals at various wavelengths. For instance, in some embodiments, the phosphor compounds of the present disclosure emit luminescence signals in the blue-green region of the electromagnetic spectrum. In some embodiments, the phosphor compounds emit luminescence signals in the blue region of the electromagnetic spectrum.

In more specific embodiments, the phosphor compounds absorb light in the ultraviolet (UV) to near UV region (~365 nm to 410 nm) and re-emit the absorbed light in the blue region (~440 nm to ~475 nm) of the electromagnetic spectrum.

Luminescence signals emitted from phosphor compounds may be detected in various manners. For instance, in some embodiments, the detection occurs visually. In some embodiments, the detection occurs at designated times or at a single time. In some embodiments, the detection occurs in real-time.

In some embodiments, the detection can occur by the use of a detection device. For instance, in some embodiments, the detection device includes, without limitation, a film-based camera, a digital camera, a luminometer, a fluorometer, a spectrophotometer, a portable electronic device, and combinations thereof. In some embodiments, the detection device is a spectrophotometer. In some embodiments, the detection device is a digital camera, such as a film-based digital camera (e.g., a digital camera with a CMOS, CCD or other type of sensor).

In some embodiments, the detection device is a portable electronic device. In some embodiments, the portable electronic device includes, without limitation, a cell phone, a smart phone, a tablet, a personal digital assistant, a laptop, and combinations thereof.

In some embodiments, the detection of luminescence signals emitted from phosphor compounds occurs in a qualitative manner. In some embodiments, the detection occurs in a quantitative manner such that the amount of the analyte in the sample is quantified. In some embodiments, the detection occurs by measuring the luminescence signal from the phosphor compound in order to allow detection or quantification of the analyte.

In some embodiments, the detection occurs by measuring the luminescence signal intensity from the phosphor compound in order to allow detection or quantification of the analyte. In some embodiments, the luminescence signal intensity can be measured on a scale from 0 pixels to 250 pixels (e.g., as demonstrated in FIGS. 10 and 11).

Correlating Luminescence Signal to Analytes

Various methods may be utilized to correlate a luminescence signal to the presence or absence of an analyte. For instance, in some embodiments, the absence of a luminescence signal indicates the absence of the analyte from the sample. In some embodiments, the presence of the luminescence signal indicates the presence of the analyte in the sample.

In some embodiments, the correlation can utilize the use of color differentiation methods. For instance, in some embodiments, the presence of a specific emission color will indicate the presence of a specific target analyte. In some embodiments, the methods of the present disclosure can be designed so that each analyte is associated with a specific phosphor emission color. In some embodiments, the presence of multiple phosphor emission colors can be identified concurrently to indicate the presence of multiple analytes in a single sample. In some embodiments, the color of the emission signal can be blue-emitting or non-blue-emitting, such as a green-emitting or blue-green emitting persistent phosphor compound.

In some embodiments, the correlation step can utilize various detection devices that were described previously. For instance, in some embodiments, the detection of a luminescence signal can utilize a film-based camera, a digital camera, a luminometer, a fluorometer, a spectrophotometer, a portable electronic device such as a smart phone, and combinations thereof.

Detection of Multiple Analytes

In some embodiments, the methods of the present disclosure can be utilized to detect a single analyte in a sample. In some embodiments, the methods of the present disclosure can be utilized to detect multiple analytes in a sample in parallel. In some embodiments, the surface includes analyte binding agents for each of the analytes to be detected in the sample. In some embodiments, the composition includes a plurality of different phosphor compounds that are each specific for an analyte to be detected in the sample.

Detection Environments

The methods of the present disclosure can occur in various environments. For instance, in some embodiments, the detection occurs in vitro. In some embodiments, the detection occurs in a diagnostic setting, such as sensitive point-of-care diagnostic settings.

In some embodiments, the methods of the present disclosure may be practiced through the use of various assays. For instance, in some embodiments, the methods of the present disclosure may utilize assays that include, without limitation, lateral flow assays, surface-bound assays, in flow through assays, assays associated with buoyant materials, assays associated with magnetic materials for concentration or force stringency, and combinations thereof.

APPLICATIONS AND ADVANTAGES

In some embodiments, the phosphor compounds of the present disclosure emit in the blue-green region of the electromagnetic spectrum when excited with a solid state white light (e.g., a smartphone-based flash) have high photoluminescence quantum yields, have a long luminescence lifetime, and are chemically robust in aqueous environments. In combination, the aforementioned properties allow the phosphor compounds of the present disclosure to be used as optical reporters in accordance with the methods of the present disclosure.

Moreover, the methods of the present disclosure have several advantages over existing phosphorescent reporter technologies. For instance, in some embodiments, the emission wavelength of the phosphor compounds can be varied incrementally without affecting the long lifetime of the phosphor compositions. Moreover, the aforementioned advantages allow chemical control of the optical properties of the phosphor compounds such that the phosphor compounds can be optimized for a range of applications that require a blue persistent phosphor.

Furthermore, limiting the green component of the phosphor compounds of the present disclosure can allow for the development of multiplexing lateral flow assays. For instance, in some embodiments, $(Sr_{1-\delta}Ba_{\delta})_2MgSi_2O_7:Eu^{2+}$ can be combined with $SrAl_2O_4:Eu^{2+}, Dy^{3+}$ for smartphone-based time-gated imaging.

ADDITIONAL EMBODIMENTS

Reference will now be made to various embodiments of the present disclosure and experimental results that provide support for such embodiments. Applicants note that the disclosure herein is for illustrative purposes only and is not intended to limit the scope of the claimed subject matter in any way.

Example 1. Optimizing Blue Persistent Luminescence in $(Sr_{1-\delta}Ba_\delta)_2MgSi_2O_7$:$Eu^{2+}$, $Dy^{3+}$ Via Solid Solution for Use in Point-of-Care Diagnostics In this Example, the development of persistent phosphors for use in lateral flow assays (LFA) was demonstrated for the solid solution $(Sr_{1-\delta}Ba_\delta)_2MgSi_2O_7$:$Eu^{2+}$, $Dy^{3+}$ ($\delta$=0, 0.125, 0.25, 0.375), which is prepared using a high-temperature solid-state reaction as confirmed by synchrotron X-ray powder diffraction (other synthetic methods, such as sol-gel reactions, can also be utilized to synthesize the aforementioned persistent phosphors). The substitution of barium for strontium enables control over the $Eu^{2+}$ 5d-orbital crystal field splitting (CFS) as a tool for tuning the emission wavelength while maintaining luminescence lifetimes for more than 9 minutes across the composition range. Thermoluminescence measurements of the solid solution provide evidence that trap states contribute to the persistent lifetimes with the trap depths also remaining constant as a function of composition. Time-gated luminescence images of these compounds are captured on a smartphone arranged in a layout to mimic a point-of-care test and demonstrate the viability of using these materials as optical reporters. Moreover, comparing the blue-emitting $(Sr_{0.625}Ba_{0.375})_2MgSi_2O_7$:$Eu^{2+}$, $Dy^{3+}$ and the green-emitting $SrAl_2O_4$:$Eu^{2+}$, $Dy^{3+}$ in a single LFA-type format shows these two compounds can be detected and resolved simultaneously, thereby permitting the development of a multiplexed LFA.

Example 1.1. Sample Preparation

Polycrystalline powders with the nominal compositions $[(Sr_{1-\delta}Ba_\delta)_{1.99} Eu_{0.01}]MgSi_2O_7$ and $[(Sr_{1-\delta}Ba_\delta)_{1.96} Eu_{0.01} Dy_{0.03}]MgSi_2O_7$ ($\delta$=0, 0.125, 0.250, 0.375) were synthesized via high temperature solid state synthesis using the following starting reagents: $SrCO_3$ (Alfa Aesar 98%), $BaCO_3$ (Johnson Mathey 98%), MgO (Sigma-Aldrich 99.99%), $SiO_2$ (Sigma-Aldrich 99.5%), $Eu_2O_3$ (Materion Advanced Chemicals 99.9%), and $Dy_2O_3$ (Sigma-Aldrich 99.99%). Additionally, a 5 wt % of boric acid (Sigma-Aldrich 99.98%) was incorporated as a flux. All powders were first ground with an agate mortar and pestle for approximately 30 minutes and then placed in a shaker mill (Spex 8000M) for 30 minutes. The mixtures were heated in a reducing atmosphere of 5% $H_2$/95% $N_2$ at 1150° C. for 6 hours with heating and cooling ramp rates of 3° C./min. They were subsequently ground and annealed at 1000° C. for 4 hours with the same reducing atmosphere and ramp rates as the initial heating.

Example 1.2. X-Ray Diffraction

Phase pure samples were confirmed using high-resolution synchrotron X-ray powder diffraction at room temperature with a calibrated wavelength of $\lambda$=0.414221 Å using beamline 11-BM at the Advanced Photon Source, Argonne National Laboratory.

Crystallographic data were determined by Rietveld refinements using the general structural analysis system (GSAS). A shifted Chebyshev function was used to calculate the background, while a pseudo-Voigt function was used for determining peak shape.

Example 1.3. Optical Characterization

Emission and excitation spectra and persistent luminescence (PersL) lifetimes were measured at room temperature with 75 W xenon arc lamp steady state fluorimeter (PTI Instruments). For the PersL lifetimes, samples were heated to 150° C. and cooled to room temperature in the dark followed by irradiation with an excitation wavelength of 365 nm for 10 minutes followed by a 30 second delay after the excitation source was turned off. Upon opening the shutter, the samples were measured with an emission wavelength of 460 nm for one hour. PersL lifetimes were determined from an average of three independent sample measurements.

Thermoluminescence was conducted by placing samples in a Janis cryostat (VPF-100) to control the temperature between 100 K and 500 K. The samples were isolated in total darkness for a minimum of 12 hours and initially heated to 500 K to ensure all trap states were emptied and then allowed to cool to room temperature. The cryostat was then cooled to 100 K and then the sample was irradiated for 10 minutes at 365 nm using a Xe arc lamp. Upon turning off the lamp, a 30 second delay was used before the cryostat was ramped to 500 K with a ramp rate of 5 K/min. The thermoluminescence emission was measured at 465 nm.

Example 1.4. Time-Gated Smartphone Imaging

A software application developed for the iOS 9 smartphone platform was used to image the samples. An APPLE® IPHONE® 5 smartphone was used with camera settings of ISO 2000, an irradiation time of 3.3 seconds followed by a 100 millisecond delay. Five images were captured in a cycle and averaged together. Image processing tools in MATLAB 2015a and an in-house developed script were used to evaluate the red, green, and blue channel intensity profiles of each sample.

Example 1.5. Structure Solution for $(Sr_{1-\delta}Ba_\delta)_2MgSi_2O_7$ ($\delta$=0, 0.125, 0.25, 0.375)

Figure 2A:
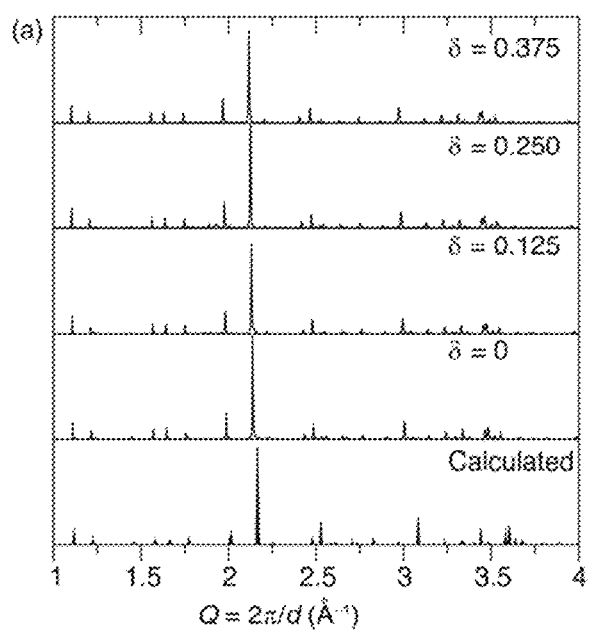
FIGS. 2A and 2B show Synchrotron X-ray powder diffraction data for $(Sr_{1-\delta}Ba_\delta)_2MgSi_2O_7$ ($\delta=0$, 0.125, 0.250, 0.375), showing that the solid solution can be prepared phase pure (FIG. 2A). Also shown is a Rietveld refinement for $\delta=0$ (FIG. 2B). Experimental data is black, refinement is orange, and the difference is blue. The rare-earth ions were excluded in the refinement due to their low substitution concentration.

Strontium magnesium disilicate crystallizes in tetragonal space group $P\bar{4}2_1m$ (no. 113), with the Åkermanite structure type. Substituting $Ba^{2+}$ for $Sr^{2+}$ in the crystal structure forms a solid solution following $(Sr_{1-\delta}Ba_\delta)_2MgSi_2O_7$:$Eu^{2+}$ ($\delta$=0, 0.125, 0.25, 0.375), which can be achieved via solid state synthesis. Synchrotron X-ray powder diffraction, shown in FIG. 2A, confirms the entire solid solution is phase pure with the exception of an unidentified, minor impurity in the $\delta$=0.25 sample. The crystal structure is maintained across this range with the expected shift in the lattice parameters to smaller Q-spacing following the larger unit cell volume with increasing $Ba^{2+}$ concentration. Previous reports of this solid solution suggest the crystal structure will maintain the tetragonal space group up to 80% $Ba^{2+}$ substitution before converting to the monoclinic space group. Samples with 50% and 75% $Ba^{2+}$ were also synthesized here. The sample with 50% $Ba^{2+}$ formed the tetragonal space group as expected although subsequent photoluminescence measurements showed an anomalous broad emission peak with a specific increase in the green portion of the visible spectrum while the 75% Ba concentration did not form the tetragonal space group. Thus, the composition range of the samples examined in this Example was limited to $0 \leq \delta \leq 0.375$.

Figure 2B:
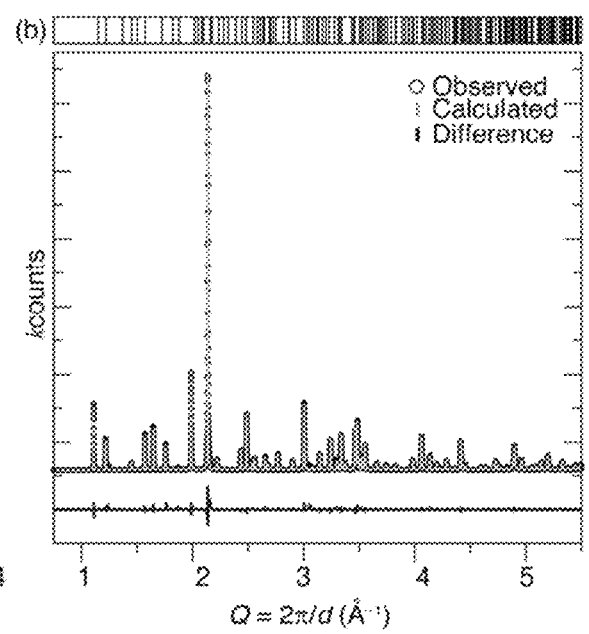

A Rietveld refinement of all phases prepared produces the crystallographic parameters with the $Sr_2MgSi_2O_7$:$Eu^{2+}$ results listed in Table 1 and Table 2 and the refinement is plotted in FIG. 2B. The data for the remaining compositions are provided in Tables 3-4.

TABLE 1

Rietveld Refinement Data of $Sr_2MgSi_2O_7$ using 11-BM Synchrotron Radiation. The rare-earth ions were excluded in the refinement due to their low substitution concentration.

| Formula | $Sr_2MgSi_2O_7$ |
|---|---|
| Radiation type; λ (Å) | 11-BM; 0.414221 |
| 2θ range (deg) | 0.5-49.95 |
| Temperature (K) | 295 |
| Space group; Z | $P\bar{4}2_1m$ (No. 113); 2 |
| Lattice parameters | |
| a (Å) | 8.0071(1) |
| c (Å) | 5.1674(2) |
| Volume (Å³) | 331.30(1) |
| Calculated Density (g cm⁻³) | 3.686 |
| Formula weight (g mol⁻¹) | 735.420 |
| $R_p$ | 0.0829 |
| $R_{wp}$ | 0.1179 |
| $\chi^2$ | 4.453 |

TABLE 2

Atomic Coordinates and Isotropic Displacement Parameters of $Sr_2MgSi_2O_7$: $Eu^{2+}$ as determined by Rietveld Refinement of 11-BM Synchrotron X-ray Diffraction Data. The rare-earth ions were excluded in the refinement due to their low substitution concentration.

| Atom | Wyck. site | x | y | z | $U_{iso}$ (Å²) |
|---|---|---|---|---|---|
| Sr | 4e | 0.3345(3) | 0.1655(3) | 0.5078(9) | 0.0087(6) |
| Mg | 2a | 0 | 0 | 0 | 0.006(3) |
| Si | 4e | 0.1381(9) | 0.3620(9) | 0.943(2) | 0.011(3) |
| O(1) | 2c | 1/2 | 0 | 0.156(7) | 0.013(1) |
| O(2) | 4e | 0.140(2) | 0.360(2) | 0.255(4) | 0.020(7) |
| O(3) | 8f | 0.079(2) | 0.188(2) | 0.7978(4) | 0.010(4) |

TABLE 3

Rietveld Refinement of $(Sr_{1-\delta}Ba_\delta)_2MgSi_2O_7$ (δ = 0.125, 0.25, 0.375) using Synchrotron Radiation.

| Formula | $(Sr_{0.875}Ba_{0.125})_2MgSi_2O_7$ | $(Sr_{0.75}Ba_{0.25})_2MgSi_2O_7$ | $(Sr_{0.625}Ba_{0.375})_2MgSi_2O_7$ |
|---|---|---|---|
| Radiation type, λ (Å) | | 11-BM 0.414221 | |
| 2θ range (deg) | | 0.5-50 | |
| Temperature (K) | | 295 | |
| Space group; Z | | $P\bar{4}2_1m$ (No. 113), 2 | |
| Lattice parameters | | | |
| a (Å) | 8.0249(4) | 8.0447(2) | 8.0687(1) |
| c (Å) | 5.1831(3) | 5.2037(3) | 5.2296(2) |
| Volume (Å³) | 333.79(2) | 336.77(2) | 340.47(1) |
| Calculated Density (g cm⁻³) | 3.785 | 3.827 | 3.929 |
| Formula weight (g mol⁻¹) | 760.90 | 776.063 | 805.601 |
| $R_p$ | 0.0974 | 0.1110 | 0.0703 |
| $R_{wp}$ | 0.1520 | 0.1538 | 0.0917 |
| $\chi^2$ | 7.967 | 4.911 | 3.311 |

TABLE 4

Atomic Coordinates, Isotropic Displacement Parameters, and Occupancies as Determined by Rietveld Refinement of 11-BM Synchrotron X-ray Diffraction Data

| Atom | Wyckoff position | x | y | z | Occupancy | $U_{iso}$ (Å²) |
|---|---|---|---|---|---|---|
| (a) $(Sr_{0.875}Ba_{0.125})_2MgSi_2O_7$ | | | | | | |
| Sr | 4e | 0.3344(4) | 0.1656(4) | 0.5089(1) | 0.872(2) | 0.0058(8) |
| Ba | 4e | 0.3344(4) | 0.1656(4) | 0.5089(1) | 0.128(2) | 0.0441(8) |
| Mg | 2a | 0 | 0 | 0 | 1 | 0.0070(5) |
| Si | 4e | 0.1368(1) | 0.3632(1) | 0.9420(3) | 1 | 0.0123(4) |
| O(1) | 2c | 1/2 | 0 | 0.142(1) | 1 | 0.025(2) |
| O(2) | 4e | 0.1415(4) | 0.3585(4) | 0.2470(7) | 1 | 0.029(1) |
| O(3) | 8f | 0.0784(3) | 0.1855(3) | 0.7975(5) | 1 | 0.011(6) |
| (b) $(Sr_{0.75}Ba_{0.25})_2MgSi_2O_7$ | | | | | | |
| Sr | 4e | 0.3346(4) | 0.1645(4) | 0.5087(1) | 0796(6) | 0.00810(9) |
| Ba | 4e | 0.3346(4) | 0.1645(4) | 0.5087(1) | 0.204(6) | 0.00810(9) |
| Mg | 2a | 0 | 0 | 0 | 1 | 0.0067(6) |
| Si | 4e | 0.1368(1) | 0.3632(1) | 0.9450(3) | 1 | 0.0066(5) |
| O(1) | 2c | 1/2 | 0 | 0.150(1) | 1 | 0.014(2) |
| O(2) | 4e | 0.1380(3) | 0.3620(3) | 0.2553(6) | 1 | 0.010(1) |
| O(3) | 8f | 0.0804(3) | 0.1885(3) | 0.8096(5) | 1 | 0.0108(7) |
| (c) $(Sr_{0.625}Ba_{0.375})_2MgSi_2O_7$ | | | | | | |
| Sr | 4e | 0.3342(2) | 0.1657(2) | 0.5091(8) | 0.655(4) | 0.00850(6) |
| Ba | 4e | 0.3342(2) | 0.1657(2) | 0.5091(8) | 0.345(4) | 0.00850(6) |
| Mg | 2a | 0 | 0 | 0 | 1 | 0.0049(3) |

TABLE 4-continued

Atomic Coordinates, Isotropic Displacement Parameters, and Occupancies as Determined by Rietveld Refinement of 11-BM Synchrotron X-ray Diffraction Data

| Atom | Wyckoff position | x | y | z | Occupancy | $U_{iso}$ (Å$^2$) |
|---|---|---|---|---|---|---|
| Si | 4e | 0.1368(1) | 0.3630(9) | 0.9477(2) | 1 | 0.0086(3) |
| O(1) | 2c | 1/2 | 0 | 0.1498(6) | 1 | 0.0078(9) |
| O(2) | 4e | 0.1381(2) | 0.3619(2) | 0.2466(4) | 1 | 0.0155(8) |
| O(3) | 8f | 0.0776(2) | 0.1915(2) | 0.8128(3) | 1 | 0.0137(5) |

Figure 3:
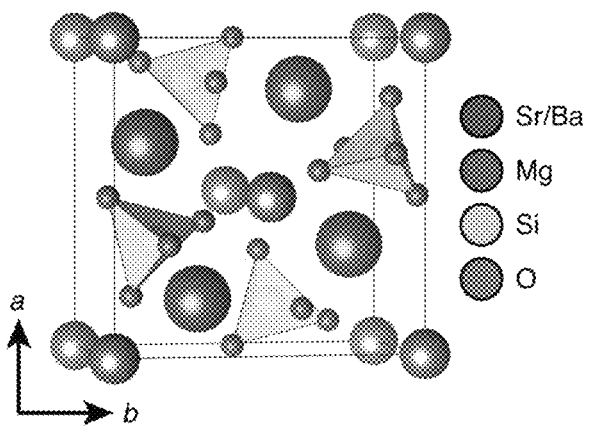
FIG. 3 shows a crystal structure of $(Sr_{1-\delta}Ba_\delta)_2MgSi_2O_7$ by Rietveld refinement with $SiO_4$ tetrahedral highlighted.

All of the refinements are in agreement with the previously reported crystal structure. The unit cell, shown in FIG. 3, contains alternating [SiO$_4$] tetrahedral and [MgO$_4$]tetrahedral that are corner connected to form layers of five-membered rings. These layers stack along the c-direction creating two dimensional sheets of polyhedral units. The structure also contains only one crystallographic site for Sr$^{2+}$ that sits between the [SiO$_4$] and [MgO$_4$] layers and is coordinated by 8 oxygen atoms, three of which are crystallographically independent on Wyckoff site 4e. The presence of only one alkaline-earth cation site in the crystal structure is ideal for phosphors because it tends to produce a narrow spectral emission. Moreover, this crystal structure and coordination environment provides an adequate setting for substitution of Ba$^{2+}$ on to the Sr$^{2+}$ site.

Figures 4A, 4B:
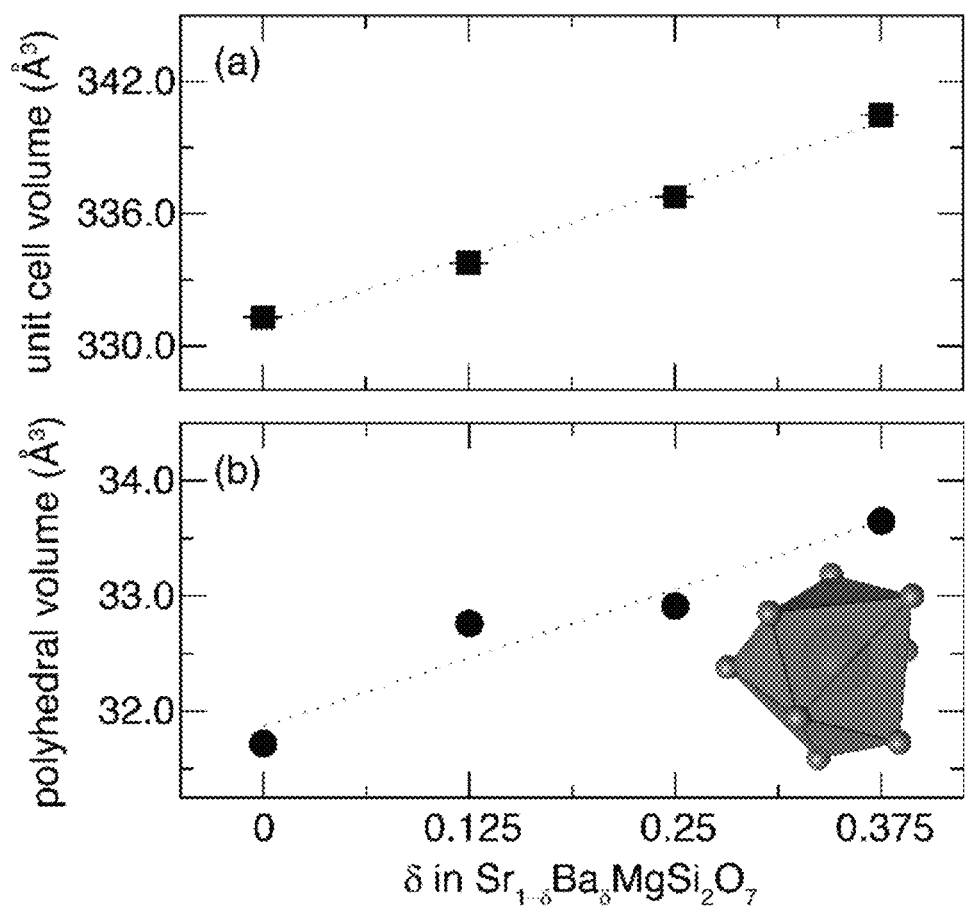
FIGS. 4A and 4B show that unit cell volume (FIG. 4A) and polyhedral volume (FIG. 4B) increase linearly with $Ba^{2+}$ concentration. The (Sr/Ba)—O coordination environment is also shown.

The unit cell volume of the solid solution follows Végard's law (FIG. 4A) with the lattice parameters and cell volume increasing linearly as the larger Ba$^{2+}$ ($r_{8\text{-}coord}$=1.42 Å) is substituted onto the smaller Sr$^{2+}$ site ($r_{8\text{-}coord}$=1.26 Å). The most significant change in the crystal structure arises in the polyhedral volume of the Sr$^{2+}$/Ba$^{2+}$ cation site. As shown in FIG. 4B, the unit cell volume increase is dictated entirely by the substitution of the larger Ba$^{2+}$ cation in the [SrO$_8$] polyhedral while the [SiO$_4$] and [MgO$_4$] polyhedral units remain constant regardless of δ. The increase in average (Sr/Ba)—O bond length from δ=0 to δ=0.375 is 2.12%, which is comparable to the change in unit cell volume. The largest increase occurs for the (Sr/Ba)—O(3) bond with a 3% increase across the substitution range, while the smallest change in bond length is the (Sr/Ba)—O(2) contact. This increase in bond length with the addition of Ba$^{2+}$ will affect crystal field splitting and ultimately change the luminescent properties of Eu$^{2+}$ in the crystal structure.

Example 1.6. Photoluminescence

The substitution of Eu$^{2+}$ for Sr$^{2+}$/Ba$^{2+}$ as the luminescent center is ideal in this crystal system to induce optical properties because the atoms are isovalent and similar in ionic size. Incorporating Eu$^{2+}$ as the luminescent center in Sr$_2$MgSi$_2$O$_7$:Eu$^{2+}$ produces an excitation maximum wavelength ($\lambda_{ex}$) at approximately 365 nm that in turn generates an efficient photon emission with a maximum wavelength ($\lambda_{em}$) at 470 nm.

Figure 5A:
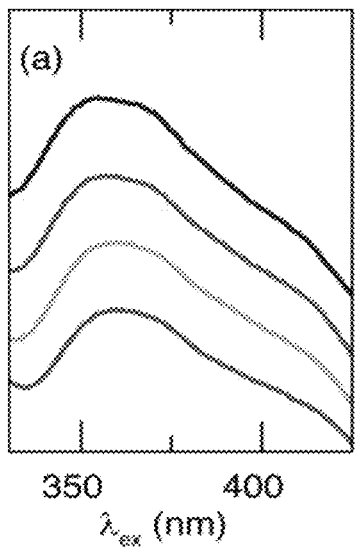
FIGS. 5A, 5B and 5C show the excitation spectra (FIG. 5A), the emission spectra (FIG. 5B), and the Gaussian fit diagram (FIG. 5C) for $(Sr_{1-\delta}Ba_\delta)_{2-x}MgSi_2O_7:Eu^{2+}$ ($\delta=0$, 0.125, 0.250, 0.375). Emission spectra were collected at $\lambda=365$ nm and the excitation spectra were collected at the $\lambda_{max}$ of emission spectrum for each sample. The Gaussian fit is solid gray. The CIE diagram in FIG. 5C shows blue shift and reduction in green emission.
Figure 5B:
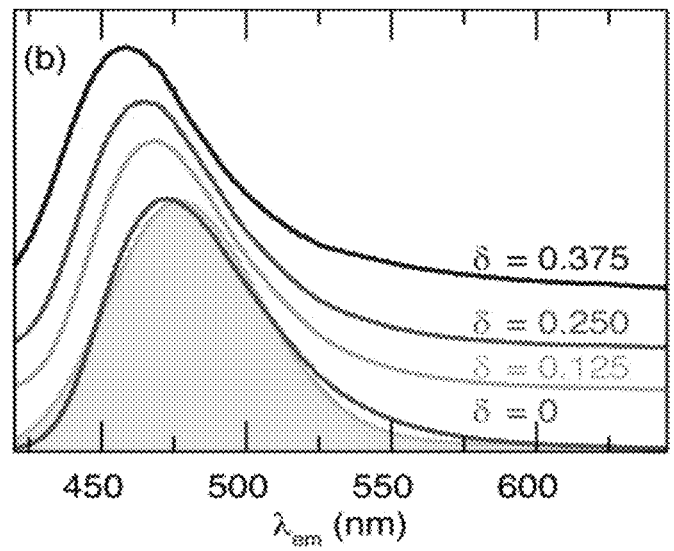
Figure 5C:
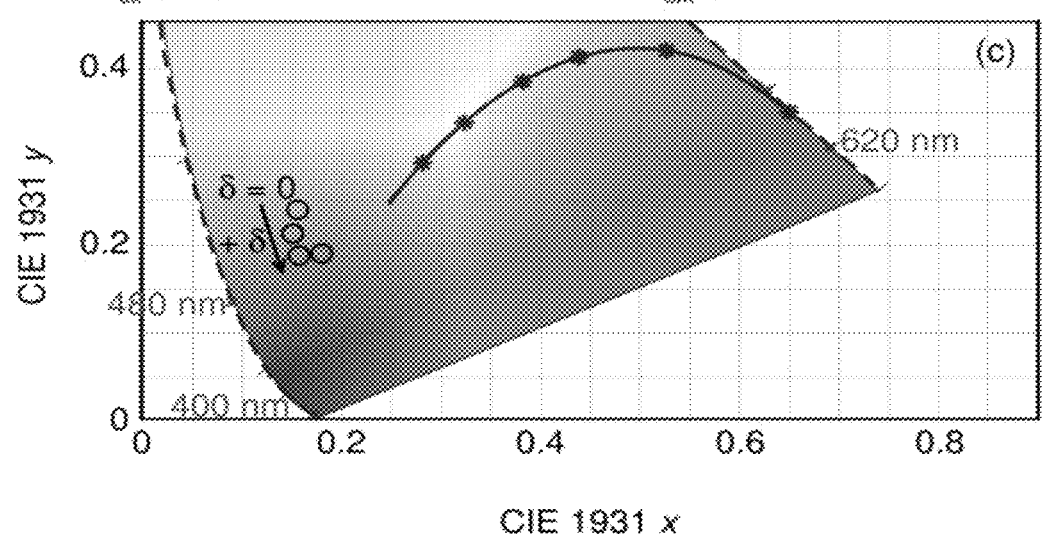

FIG. 5A shows the excitation spectra of the solid solution changes minimally upon the addition of Ba$^{2+}$ while FIG. 5B shows that when excited with a $\lambda_{ex}$=365 nm there is an observable blue shift in the emission wavelength from $\lambda_{em}$=472 nm (δ=0) to $\lambda_{em}$=460 nm (δ=0.375). The emission corresponds to the relaxation from the Eu$^{2+}$ 5d excited state to the 4f ground state ($^2D_j \rightarrow {}^8S_{7/2}$) of a single luminescent center. Plotting the color points of this solid solution on a Commission Internationale de l'Eclairage (CIE) diagram (FIG. 5C) further supports the significant blue-shift with the addition of Ba$^{2+}$. Because Ba$^{2+}$ is larger than Sr$^{2+}$ there will be an increase in bond lengths around the luminescent center. This increase leads to a decrease in the crystal field splitting of the Eu$^{2+}$ 5d-orbitals producing a greater separation of these states from the 4f-orbitals. Consequently, this change causes a greater energy difference between the excited state and the ground state, which gives rise to the observed shift in the emission spectra.

Figure 6:
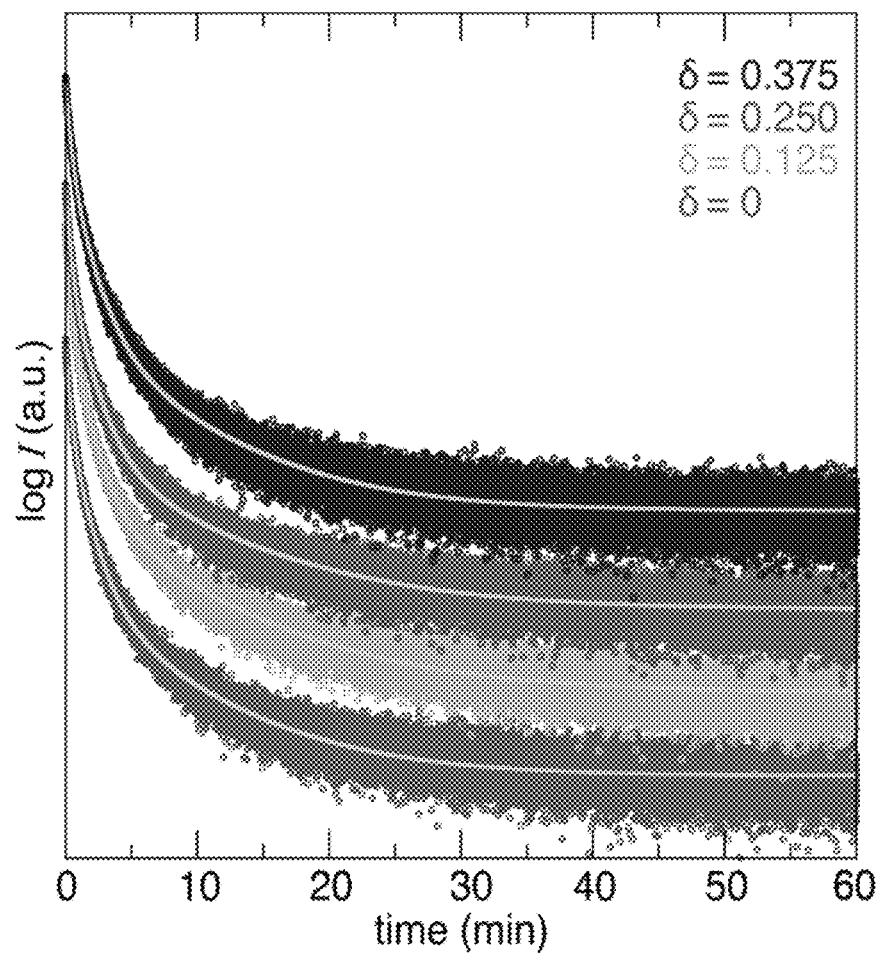
FIG. 6 shows a persistent luminescence (PersL) of $(Sr_{1-\delta}Ba_\delta)_2MgSi_2O_7:Eu^{2+}$ ($\delta=0$, 0.125, 0.250, 0.375) fit to a triple exponential. Circles indicate raw data while the solid gray line represents the fit.

Considering these compounds are known to show PersL, the effect of solid solution formation on the photon emission lifetime was also examined. The (long lifetime) decay curves for the solid solutions (FIG. 6) are analyzed according to Equation 1, where I is the normalized intensity; A$_1$, A$_2$, and A$_3$ are pre-exponential constants; $\tau_1$, $\tau_2$, and $\tau_3$ are luminescent decays and t is the time.

$$I = A_1 e^{\frac{-t}{\tau_1}} + A_2 e^{\frac{-t}{\tau_2}} + A_3 e^{\frac{-t}{\tau_3}} \quad (1)$$

Fitting to a triple exponential provided the best agreement across the entire range of data collected. Thus, three different long lifetimes are present in these compounds. Table 5 shows the decay times of $\tau_1$, $\tau_2$, and $\tau_3$ (in minutes) as the average taken from three measurements on each sample. There is very little variation in time throughout the solid solution suggesting the substitution of Ba$^{2+}$ has little effect on the PersL. These data reveal that it is possible to modify the emission color of this series of phosphors through the preparation of a solid solution without losing any of the PersL qualities.

TABLE 5

Average long lifetime decay times of (Sr$_{1-\delta}$Ba$_\delta$)$_2$MgSi$_2$O$_7$: Eu$^{2+}$.

| δ | $\tau_1$ (min) | $\tau_2$ (min) | $\tau_3$ (min) |
|---|---|---|---|
| 0 | 0.37(1) | 1.49(5) | 9.2(8) |
| 0.125 | 0.36(1) | 1.51(6) | 9.4(8) |
| 0.250 | 0.38(1) | 1.62(1) | 10.0(2) |
| 0.375 | 0.39(1) | 1.68(5) | 10(1) |

Although the PersL lifetimes occur within a desirable range for use in LFA bio-sensing applications, the intensity of the photon emission is also a factor. Therefore, to enhance the emission intensity the addition of a rare-earth co-dopant was explored. The use of co-dopants is often employed to enhance the optical properties and lifetimes of PersL phosphors, specifically the incorporation of Ce$^{3+}$, Nd$^{3+}$ and Dy$^{3+}$. In this Example, Dy$^{3+}$ was selected for co-substitution with Eu$^{2+}$ because it was determined to have a longer lifetime when compared to Ce$^{3+}$ or Nd$^{3+}$.

To ensure the presence of the trivalent rare-earth ion did not alter the optical properties relative to the Eu$^{2+}$-only compounds, the emission and excitation spectra of the Eu$^{2+}$,Dy$^{3+}$ co-substituted samples were also collected (FIGS. 7A-B). The excitation spectra of all compositions are comparable to the Eu$^{2+}$-only compounds and there are no additional peaks in the emission spectra. Likewise, the blue shift in the emission spectra is also observed as the concentration of Ba$^{2+}$ is increased. Plotting the color points for the solid solution on a CIE diagram in FIG. 7C shows that increasing Ba$^{2+}$ again causes a blue-shift in the emission spectrum.

Figure 8:
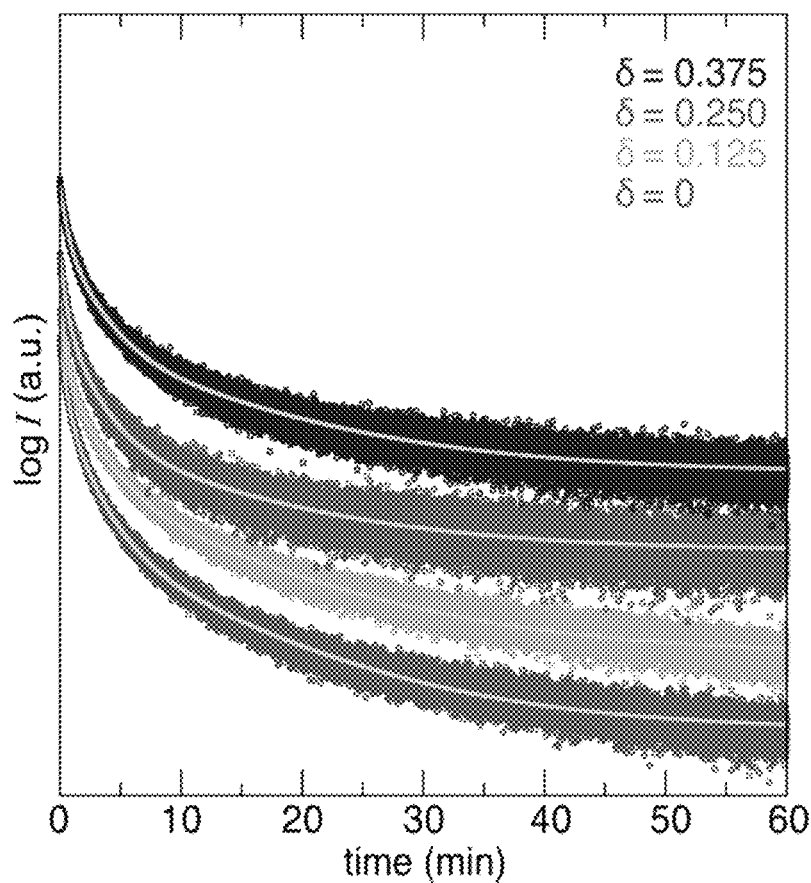
FIG. 8 shows PersL of $(Sr_{1-\delta}Ba_\delta)_{2-x}MgSi_2O_7:Eu_x^{2+}$ ($\delta=0$, 0.125, 0.250, 0.375) fit to a triple exponential. Circles indicate raw data while the solid gray line represents the fit.

The PersL for the solid solution was also fit to Equation 1 with the results shown in FIG. 8 and lifetimes given in Table 6.

TABLE 6

Average lifetime decay of
$(Sr_{1-\delta}Ba_\delta)_{2-x}MgSi_2O_7$: Eu$^{2+}$,
Dy$^{3+}$ ($\delta$ = 0, 0.125, 0.250, 0.375)
of each sample measured three times.

| $\delta$ | $\tau_1$ (min) | $\tau_2$ (min) | $\tau_3$ (min) |
|---|---|---|---|
| 0 | 0.50(2) | 2.37(5) | 12.8(1) |
| 0.125 | 0.48(3) | 2.2(2) | 12.7(7) |
| 0.250 | 0.45(8) | 2.3(2) | 12.3(8) |
| 0.375 | 0.49(2) | 2.3(1) | 12.8(7) |

The presence of Dy$^{3+}$ indeed contributes to the PersL of this material as previously reported with the average long lifetimes occurring for 3 minutes longer than the Eu$^{2+}$-only samples. Incorporating the trivalent rare-earth ion in the structure induces additional defect states that can act as luminescent trapping centers, thus increasing the long lifetime as well as the emission intensity of these materials.

Example 1.7. Thermoluminescence

To investigate the origin of the persistent luminescent lifetime, thermoluminescence (TL) measurements were conducted on the solid solutions of the Eu$^{2+}$-only and Eu$^{2+}$, Dy$^{3+}$ co-substituted samples. The presence of trap states is evident when a luminescent emission peak appears as a sample is heated at a constant rate even without concurrent excitation. The location, intensity, and shape of the peak is dependent on the heating rate, the wavelength of irradiation, and the delay between terminating the irradiation and initiating heating. To observe PersL, a trap depth should be greater than 0.4 eV at room temperature because traps shallower than this energy will detrap (empty) at lower temperatures. Alternatively, traps greater than 1 eV are considered too far below the conduction band for thermal release at room temperature. Therefore, the optimal trap depth reported for PersL at room temperature is often considered to occur at ≈0.65 eV.

In this Example, the "peak shape method" of analysis was used to quantify the trap depths from the TL peaks by deconvolution of the data using a Gaussian function ensuring the trap depths are within 5% of the actual trap depth. The location of the trap depths are determined by solving for the activation energy (E$_A$) as shown in Equation 2. Expecting second order kinetics, the values of c$_\omega$=3.54 and b$\omega$=1 were used, and k$_B$ is the Boltzmann constant. T$_m$ is the maximum temperature and, $\omega$ the full width at half maximum of the TL spectrum.

$$E_A = c_\omega \left(\frac{k_B T_m^2}{\omega}\right) - b_\omega(2kT_m) \quad (2)$$

In this Example, $\omega$ is used because it is provided by the deconvolution of the experimentally measured peaks. The full deconvolutions of all compounds prepared here are provided in Supporting Information.

Figure 9A:
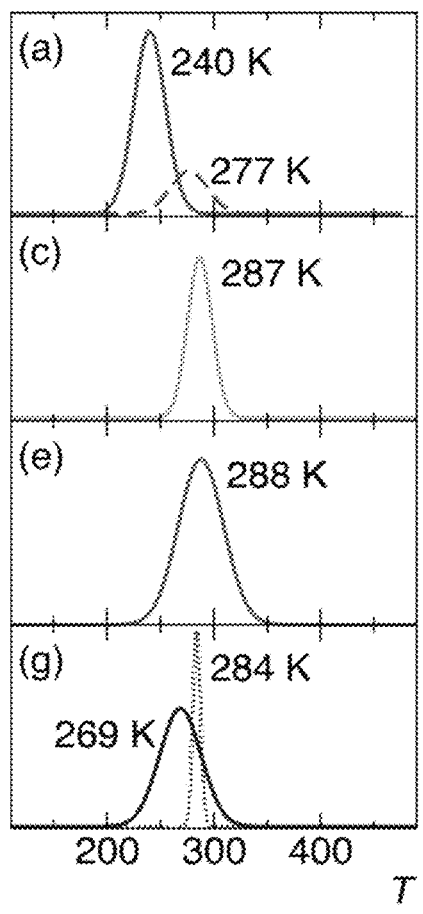
Figure 9B:
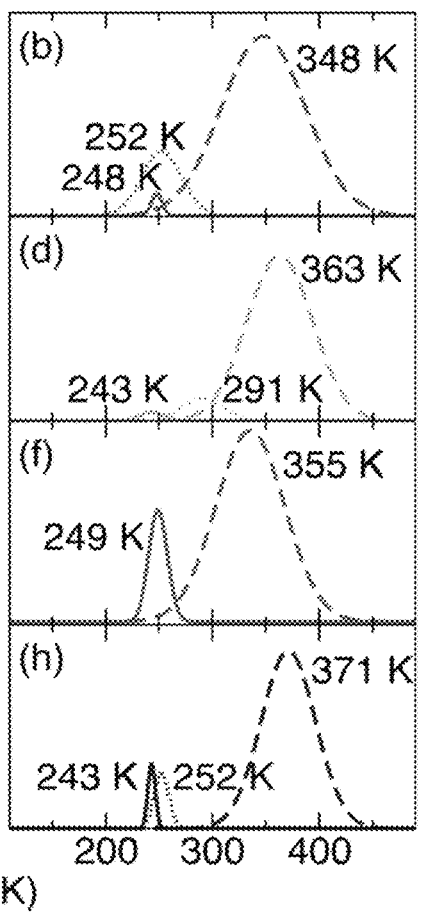

FIG. 9 shows the presence of TL peaks occurring between 240 K and 371 K, which supports that trap states are present in all of these phases and is likely the origin of PersL. The trap depths calculated from these peaks are presented in Table 7.

TABLE 7

TL peaks and their corresponding trap depths
for $(Sr_{1-\delta}Ba_\delta)_{2-x}MgSi_2O_7$ ($\delta$ = 0, 0.125, 0.250,
0.375). Eu$^{2+}$ only is shown for plots a, c, e, and g, while
Eu$^{2+}$, Dy$^{3+}$ is shown as plots b, d, f, and h.

| Plot | Temperature (K) | Trap Depth (eV) |
|---|---|---|
| a | 240 | 0.44 |
|   | 277 | 0.49 |
| b | 247 | 1.28 |
|   | 251 | 0.40 |
|   | 364 | 0.45 |
| c | 287 | 0.83 |
| d | 243 | 0.59 |
|   | 291 | 0.48 |
|   | 363 | 0.46 |
| e | 288 | 0.43 |
| f | 249 | 0.82 |
|   | 355 | 0.42 |
| g | 269 | 0.41 |
|   | 284 | 2.69 |
| h | 243 | 2.05 |
|   | 252 | 1.10 |
|   | 371 | 0.60 |

In the Eu$^{2+}$-only samples, the presence of TL peaks are likely due to intrinsic defects occurring in the crystal structure that give rise to trap states. The solid solution co-substituted with Dy$^{3+}$ has an additional peak above 300 K arising from the inclusion of Dy$^{3+}$ and is consistent with previous reports of Sr$_2$MgSi$_2$O$_7$:Eu$^{2+}$, Dy$^{3+}$. All of the phases regardless of composition produce trap depths between 0.40 eV and 0.89 eV, which is near the ideal value of ≈0.65 eV for PersL to occur at room temperature. Interestingly, when $\delta$=0.375 there are also very deep traps present, >1 eV. These should only weakly contribute to the observed PersL because the activation energy required to empty these traps is not sufficient at room temperature. Nevertheless, peak location and trap depth vary only slightly across the solid solution supporting the minor changes in PersL lifetimes with the substitution of Ba$^{2+}$ for Sr$^{2+}$. The combination of tunable emission wavelength and only minor variations in the luminescence lifetimes allows the emission color to be optimized as the optical reporter in an LFA.

Example 1.8. Smartphone-Based Time-Gated Imaging

For the incorporation of PersL phosphors as optical reporters in this point-of-care diagnostic testing format, it is preferable that the materials can be excited using a smartphone flash (usually a blue LED-based package) and that the smartphone camera can detect the PersL phosphor emission. This analysis can be completed using smartphone-based time-gated imaging, which allows a predetermined and controlled delay between the excitation of a reporter and the detection of the emission intensity. The short delay offers the ability to excite the reporter while providing adequate time for background from scattered excitation light and autofluorescence to fade before capturing the image of the reporter's luminescence. A software application designed for smartphones has been developed that sets the delay to approximately 100 ms. $SrAl_2O_4{:}Eu^{2+},Dy^{3+}$ has already been demonstrated as a successful reporter in this format and show that images captured by smartphone-based time-gated imaging require significant emission intensity at approximately one second after termination of the excitation source (the smartphone flash). The long lifetimes measured for both of the solid solutions prepared in this study indicate the emission intensity should be sufficient for detection by the smartphone-based time-gated imaging application. Measuring the photon emission with an APPLE® IPHONE® 5 smartphone (iOS 9) produced the images shown in FIG. 10. The smartphone images can then be described using an RGB color model to determine the intensity profiles of the red, blue, and green channels present during the emission.

Figure 10A:
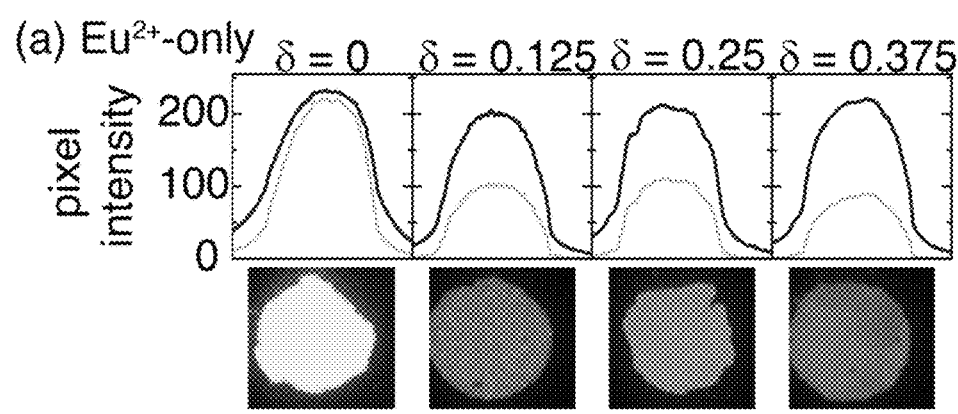
FIGS. 10A and 10B show time-gated luminescence imaging acquired with a smartphone-based bio-sensing platform and intensity profile scan for $(Sr_{1-\delta}Ba_\delta)_{2-x}MgSi_2O_7:Eu^{2+}$ (FIG. 10A) and $(Sr_{1-\delta}Ba_\delta)_{2-x}MgSi_2O_7:Eu^{2+}, Dy^{3+}$ (FIG. 10B). The blue line represents the blue channel intensity and the green line represents the green channel intensity.
Figure 10B:
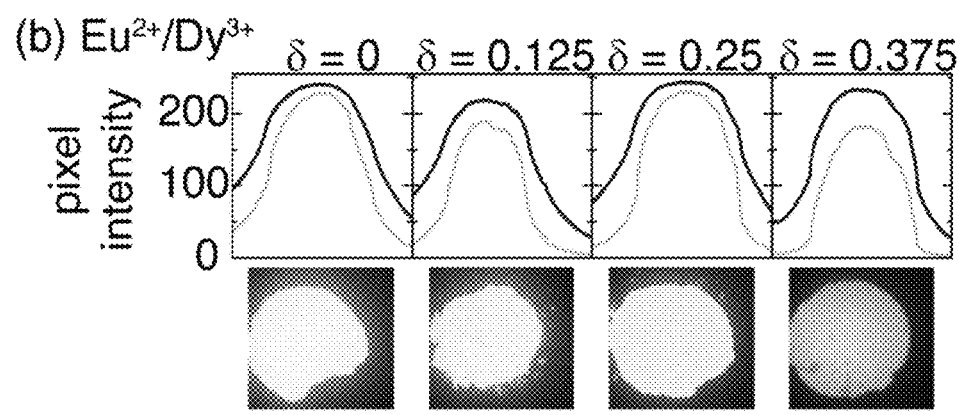
Figure 11A:
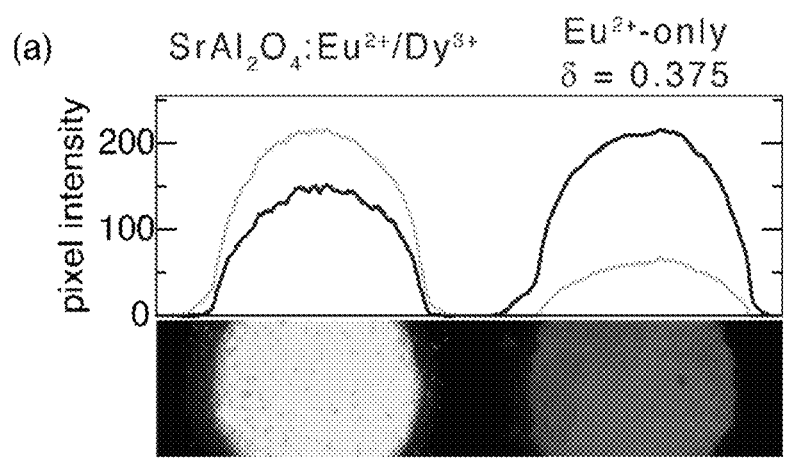
FIGS. 11A and 11B show comparisons of spectral response between $SrAl_2O_4:Eu^{2+}, Dy^{3+}$ and $(Sr_{1-\delta}Ba_\delta)_2MgSi_2O_7:Eu^{2+}$ (FIG. 11A) and $(Sr_{1-\delta}Ba_\delta)_2MgSi_2O_7:Eu^{2+}, Dy^{3+}$ (FIG. 11B) using time-gated luminescence. The images were acquired with a smartphone-based bio-sensing platform.
Figure 11B:
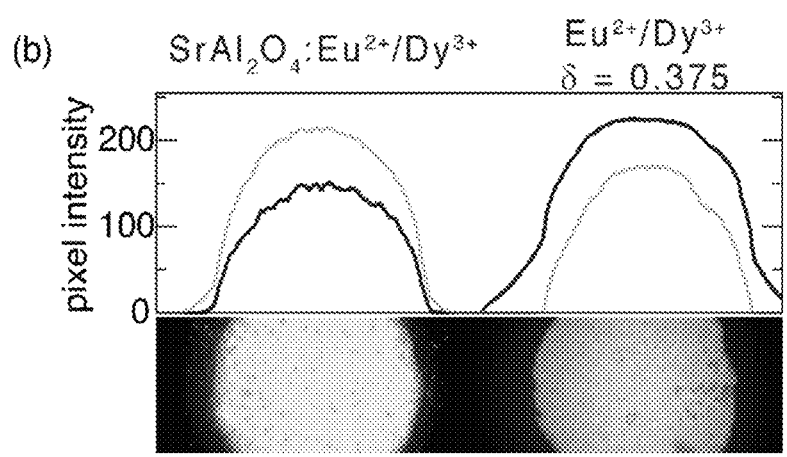
Figure 12A:
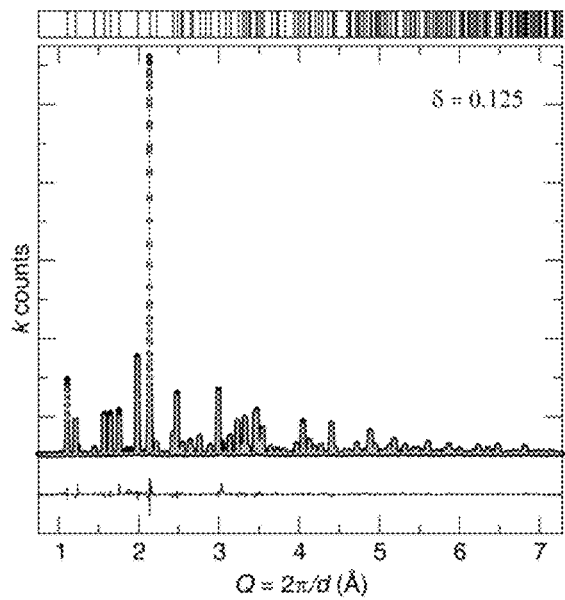
FIGS. 12A, 12B and 12C show Rietveld refinement for $(Sr_{1-\delta}Ba_\delta)_2MgSi_2O_7:Eu^{2+}, Dy^{3+}$ ($\delta$=0.125, 0.25, 0.375). Experimental data is black, refinement is orange, and the difference is blue. All are in agreement with the calculated pattern.
Figure 12B:
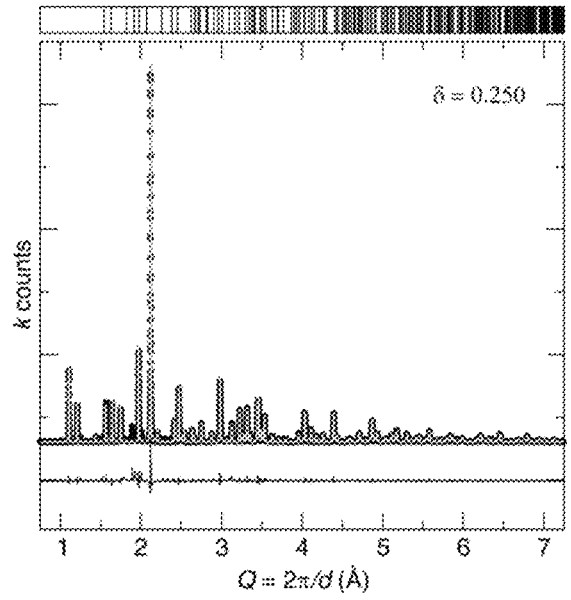
Figure 12C:
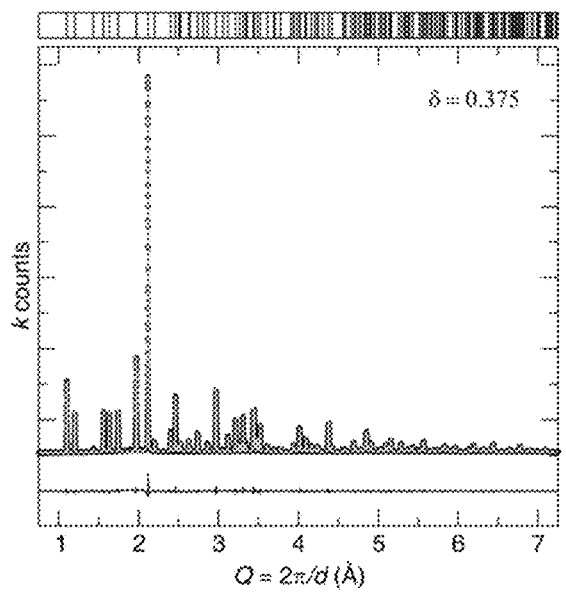
Figure 13A:
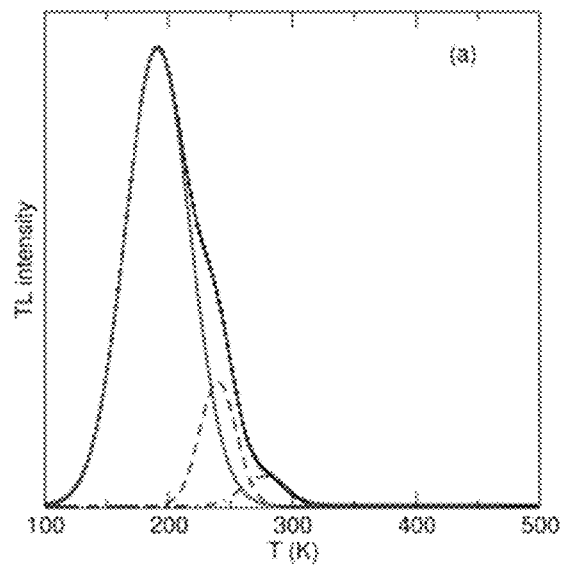
FIGS. 13A-H show thermoluminescense spectra showing the deconvolution of the trap states of $(Sr_{1-\delta}Ba_\delta)_{2-x}MgSi_2O_7$ ($\delta$=0, 0.125, 0.250, 0.375). $Eu^{2+}$ only is shown for plots in FIGS. 13A, 13C, 13E, and 13G, while $Eu^{2+},Dy^{3+}$ is shown as plots in FIGS. 13B, 13D, 13F, and 13H.
Figure 13B:
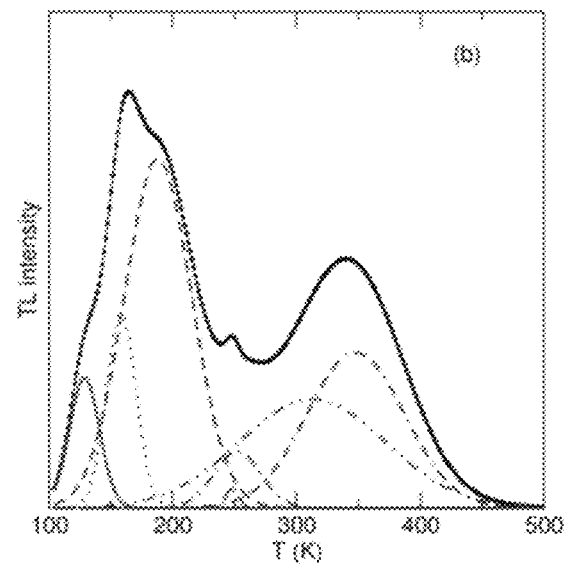
Figure 13C:
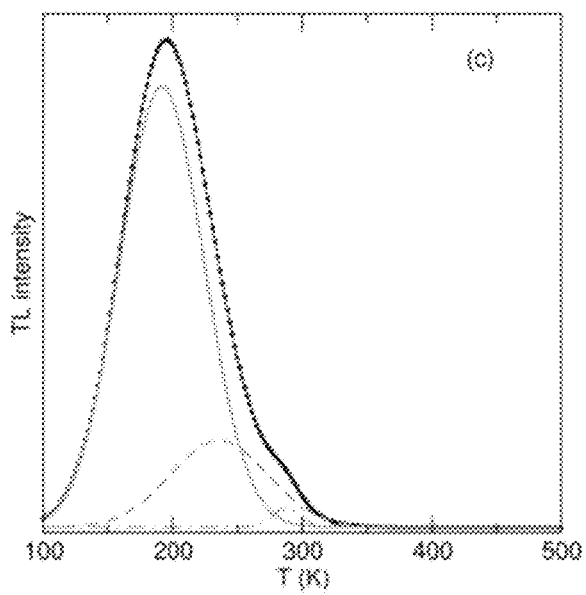
Figure 13D:
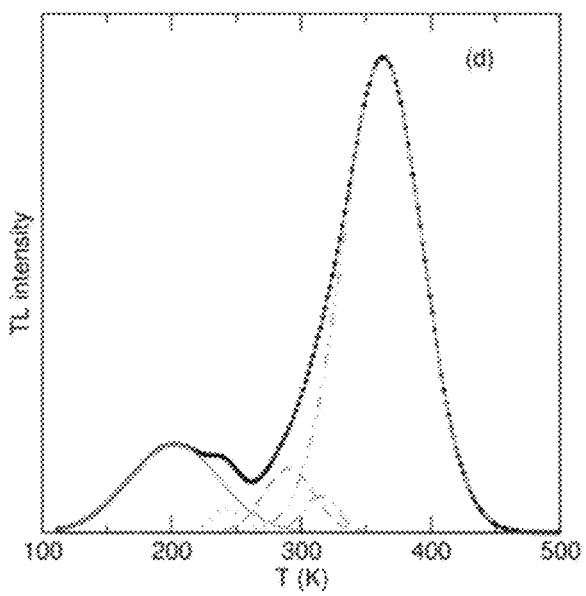
Figure 13E:
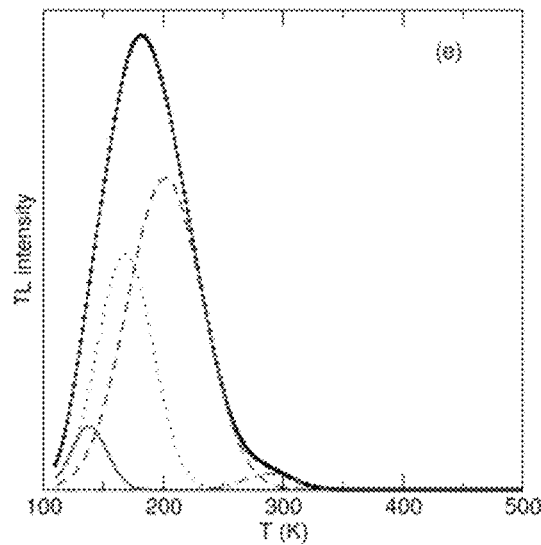
Figure 13F:
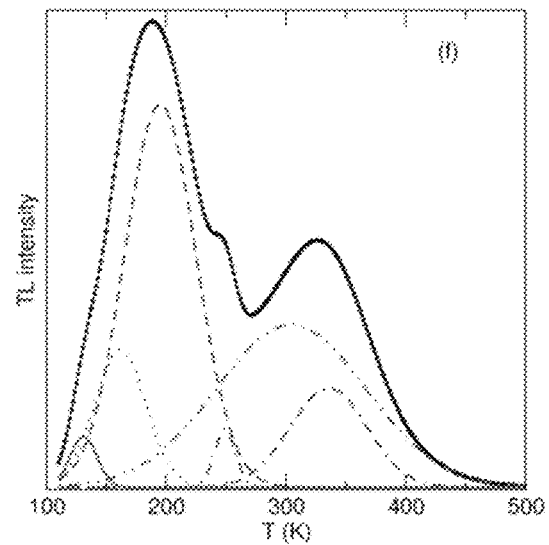
Figure 13G:
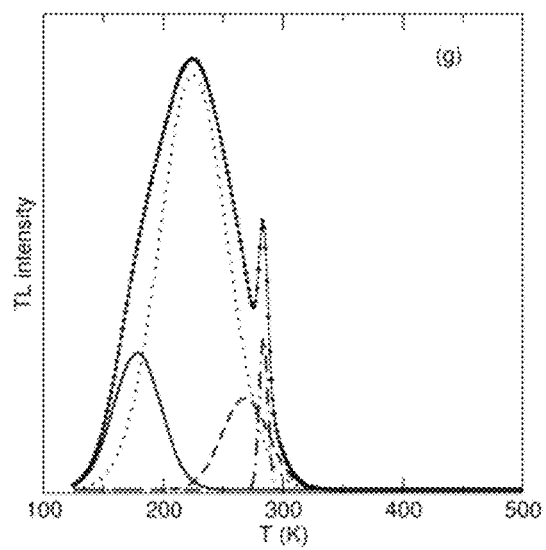
Figure 13H:
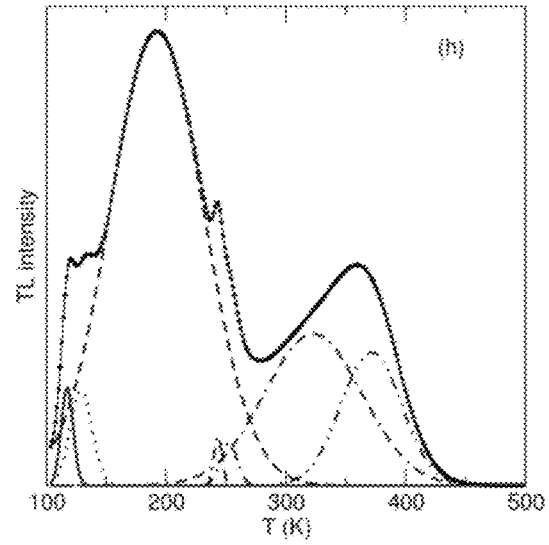

The intensity profiles of the blue and green channels of the solid solutions are also plotted in FIG. 10. The red channel has a minimal intensity in these phases and is omitted for clarity. When only $Eu^{2+}$ is substituted in the crystal structure, the green channel intensity decreases with an increase in the $Ba^{2+}$ concentration, while the blue channel retains its intensity. This is in agreement with the blue-shift in the luminescence spectrum upon incorporation of the larger $Ba^{2+}$ cation. Interestingly, the samples co-substituted with $Eu^{2+},Dy^{3+}$ also maintain the intensity of the blue channel regardless of δ. However, the decline in the green channel is only observed when δ=0.375.

The images collected by the smartphone application for each of the powder samples show the effect of reducing the green-component on the overall intensity. The compounds containing both blue and green components appear significantly brighter as the smartphone camera's spectral sensitivity varies across the visible spectrum. Consequently, replacing the bright green PersL phosphor $SrAl_2O_4{:}Eu^{2+}$, $Dy^{3+}$ would require the bright blue-green emitting $Dy^{3+}$ co-substituted samples due to their similar spectral response and equivalent brightness. However, if the desired application is multiplexing, the intensity of the green channel of the co-substituted samples may be too bright to distinguish the disilicate from $SrAl_2O_4{:}Eu^{2+},Dy^{3+}$. Thus, differentiating these two compounds in a multiplexed assay may prove difficult. This is best illustrated through a direct comparison between $SrAl_2O_4{:}Eu^{2+},Dy^{3+}$ and $(Sr_{0.625}Ba_{0.375})_2MgSi_2O_7{:}Eu^{2+}$ as well as $SrAl_2O_4{:}Eu^{2+},Dy^{3+}$ and $(Sr_{0.625}Ba_{0.375})_2 MgSi_2O_7{:}Eu^{2+},Dy^{3+}$ in a single point-of-care diagnostic test.

Simultaneously imaging $SrAl_2O_4{:}Eu^{2+},Dy^{3+}$ and $(Sr_{0.625}Ba_{0.375})_2MgSi_2O_7{:}Eu^{2+}$ (FIG. 11A) as well as $SrAl_2O_4{:}Eu^{2+},Dy^{3+}$ and $(Sr_{0.625}Ba_{0.375})_2MgSi_2O_7{:}Eu^{2+},Dy^{3+}$ (FIG. 11B) shows that the different optical properties of the two PersL phosphors can be resolved using the color profile collected by the smartphone-based time-gated imaging. $SrAl_2O_4{:}Eu^{2+},Dy^{3+}$ has a more intense green channel whereas $(Sr_{0.625}Ba_{0.375})_2MgSi_2O_7{:}Eu^{2+}$ and the co-substituted analogues have a more intense blue channel. In the case of the co-substituted samples, a significant green component remains in the emission that could make partitioning these two signals difficult. Conversely, even though the $(Sr_{0.625}Ba_{0.375})_2MgSi_2O_7{:}Eu^{2+}$ has less of a green component its overall lower intensity may limit detectability at the low concentrations of PersL phosphors used in LFAs. Nevertheless, these images and color profile scans substantiate the possibility of combining multiple phosphors in point-of-care assays adapted for use in the smartphone-based bio-sensing application.

The embodiments described herein are to be construed as illustrative and not as constraining the remainder of the disclosure in any way. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method for detection of at least one analyte of interest in a sample, wherein the method comprises:
    associating the sample with a surface comprising a first analyte binding agent, wherein the associating results in the immobilization of at least some of the analytes present in the sample on the surface;
    contacting the analyte present in the sample with a composition comprising at least one phosphor compound,
    wherein the at least one phosphor compound is linked to a second analyte binding agent,
    wherein the at least one phosphor compound is $(Sr_{1-δ}Ba_δ)_2MgSi_2O_7{:}Eu^{2+}Dy^{3+}$,
        wherein δ is between 0 and 0.375, and
        wherein the at least one phosphor compound is in the form of particles
    wherein the associating and contacting result in the formation of immobilized first analyte binding agent-analyte-second analyte binding agent-phosphor complexes on the surface;
    detecting a presence or absence of a luminescence signal from the immobilized complexes wherein the detecting comprises:
    exciting the phosphor compound with a light source;
    detecting the emitted luminescence signal from the excited phosphor compound; and
    correlating the luminescence signal to the presence or absence of the analyte in the sample.

2. The method of claim 1, wherein the associating step and the contacting step occur simultaneously.

3. The method of claim 1, wherein the associating step occurs before the contacting step.

4. The method of claim 1, wherein the contacting step occurs before the associating step.

5. The method of claim 1, wherein the associating step and the contacting step occur by methods selected from the group consisting of mixing, incubating, swapping, dipping, flowing, and combinations thereof.

6. The method of claim 1, wherein the associating step occurs by flowing the sample through the surface, and wherein the contacting step occurs by mixing the sample with the composition.

7. The method of claim 1, wherein the analyte is selected from the group consisting of nucleotides, proteins, peptides, small molecules, antigens, DNA strands, oligonucleotides, metals, metal ions, and combinations thereof.

8. The method of claim 1, wherein the phosphor compound is a blue-emitting persistent phosphor compound.

9. The method of claim 1, wherein δ is 0, 0.125, 0.25, or 0.375.

10. The method of claim 1, wherein the at least one phosphor compound is $(Sr_{0.625}Ba_{0.375})_2MgSi_2O_7:Eu^{2+}, Dy^{3+}$.

11. The method of claim 1, wherein the composition comprises additional phosphor compounds.

12. The method of claim 11, wherein the additional phosphor compound is a blue-emitting persistent phosphor compound.

13. The method of claim 11, wherein the additional phosphor compound is a blue-green-emitting persistent phosphor compound.

14. The method of claim 11, wherein the additional phosphor compound is selected from the group consisting of $[AE_2MgSi_2O_7:Eu^{2+}, [AE]Al_2O_4:Eu^{2+}, Dy^{3+}$, and combinations thereof,
wherein AE is at least one of Ca, Sr, or Ba.

15. The method of claim 11, wherein the additional phosphor compound is comprises $Sr_2MgSi_2O_7:Eu^{2+}$.

16. The method of claim 12, wherein the additional phosphor compound is $SrAl_2O_4:Eu^{2+}, Dy^{3+}$.

17. The method of claim 1, wherein the method is utilized to detect a single analyte in the sample.

18. The method of claim 1, wherein the method is utilized to detect multiple analytes in the sample.

19. The method of claim 18, wherein the surface comprises analyte binding agents for each of the analytes to be detected in the sample.

20. The method of claim 18, wherein the composition comprises a plurality of different phosphor compounds.

21. The method of claim 1, further comprising a step of separating the unbound phosphor compounds from the immobilized analyte binding agent-analyte-phosphor complexes.

22. The method of claim 21, wherein the separating comprises washing away at least some of the unbound phosphor compounds from the immobilized complexes.

23. The method of claim 1, wherein the surface comprises a shape selected from the group consisting of microfluidic chips, paper microfluidics, membranes, microplates, microbubbles for flotation, transparent surfaces, particles, and combinations thereof.

24. The method of claim 1, wherein the first and second analyte binding agents are each selected from the group consisting of antibodies, aptamers, haptens, DNA strands, oligonucleotides, and combinations thereof.

25. The method of claim 1, wherein the at least one phosphor compound is excited at wavelengths ranging from about 365 nm to about 435 nm.

26. The method of claim 1, wherein the excited at least one phosphor compound emits the luminescence signal in the blue-green region of the electromagnetic spectrum.

27. The method of claim 1, wherein the detecting occurs visually.

28. The method of claim 1, wherein the detecting occurs in real-time.

29. The method of claim 1, wherein the detecting occurs by the use of a detection device.

30. The method of claim 1, wherein the detecting comprises quantifying the analyte in the sample.

31. The method of claim 1, wherein the absence of the luminescence signal indicates the absence of the analyte from the sample, and wherein the presence of the luminescence signal indicates the presence of the analyte in the sample.

32. The method of claim 1, wherein the excited phosphor compound emits the luminescence signal in the blue-green region of the electromagnetic spectrum when excited with a solid state white light.

33. The method of claim 1, wherein the particles have sizes of less than about 1000 nm.

34. The method of claim 33, wherein the particles have sizes ranging from about 50 nm to about 1000 nm.

* * * * *